(12) United States Patent
Urakawa et al.

(10) Patent No.: US 9,133,084 B2
(45) Date of Patent: Sep. 15, 2015

(54) PROCESS FOR THE PREPARATION OF METHANOL AND METHANOL-DERIVED PRODUCTS FROM CARBON OXIDES

(71) Applicant: FUNDACIÓ INSTITUT CATALÀ D'INVESTIGACIÓ QUÍMICA (ICIQ), Tarragona (ES)

(72) Inventors: Atsushi Urakawa, Fukuoka (JP); Atul Baban Bansode, Maharastra (IN)

(73) Assignee: FUNDACIÓ INSTITUT CATALÀ D'INVESTIGACIÓ QUÍMICA (ICIQ), Tarragona (ES)

( * ) Notice: Subject to any disclaimer, the term of this patent is extended or adjusted under 35 U.S.C. 154(b) by 0 days.

(21) Appl. No.: 14/401,312

(22) PCT Filed: May 15, 2013

(86) PCT No.: PCT/EP2013/059980
§ 371 (c)(1),
(2) Date: Nov. 14, 2014

(87) PCT Pub. No.: WO2013/171239
PCT Pub. Date: Nov. 21, 2013

(65) Prior Publication Data
US 2015/0133699 A1    May 14, 2015

(30) Foreign Application Priority Data
May 15, 2012 (EP) ..................................... 12382177

(51) Int. Cl.
*C07C 29/151* (2006.01)
*C07C 41/09* (2006.01)
*C07C 29/154* (2006.01)

(52) U.S. Cl.
CPC .................................. *C07C 29/154* (2013.01)

(58) Field of Classification Search
CPC ...... C07C 29/151; C07C 29/154; C07C 41/09
USPC .................................................. 568/840, 698
See application file for complete search history.

(56) References Cited

U.S. PATENT DOCUMENTS

| | | | |
|---|---|---|---|
| 1,558,559 A | 10/1925 | Mittasch et al. | |
| 1,569,775 A | 1/1926 | Mittasch et al. | |
| 3,702,886 A | 11/1972 | Argauer et al. | |
| 4,440,871 A | 4/1984 | Lok et al. | |
| 4,477,594 A * | 10/1984 | Greene et al. | 518/700 |
| 2010/0076227 A1 * | 3/2010 | Li et al. | 568/698 |
| 2010/0088951 A1 * | 4/2010 | White et al. | 44/452 |

OTHER PUBLICATIONS

Ipatieff et al. Synthysis of Methanol from Carbon Dioxide and Hydrogen over Copper-Alumina Catalysts. Mechanism of Reaction. Journal of the American Chemical Society, 1945, vol. 67 (12), 2168-2171.*
V. N. Ipatieff, et al., Synthesis of Methanol from Carbon Dioxide and Hydrogen over Copper-Alumina Catalysts. Mechanism of Reaction, Journal of the American Chemical Society, Dec. 1945, pp. 2168-2171, vol. 67, American Chemical Society, New York, NY, USA.
F. Pontzen, et al., CO2-based methanol and DME—Efficient technologies for industrial scale production, Catalysis Today, available on line Jul. 2, 2011, pp. 242-250, vol. 171, Elsevier, Amsterdam, NL.
Tian-Sheng Zhao, et al., A novel low-temperature methanol synthesis method from CO/H2/CO2 based on the synergistic effect between solid catalyst and homogeneous catalyst, Catalysis Today, available on line Aug. 18, 2009, pp. 98-104, vol. 149, Elsevier, Amsterdam, NL.
Prasert Reubroycharoen, et al. "Methanol Synthesis in Inert or Catalytic Supercritical Fluid". Fischer-Tropsch Synthesis, Catalysts and Catalysis, Studies in Surface Science and Catalysis, published Nov. 2006, copyright 2007, pp. 367-378, vol. 163, Elsevier, Amsterdam, NL.
M. Lok, edited by K.P. De Jong, Chapter 7, Coprecipitation, Synthesis of Solid Catalysts, 2009 (the year of publication is sufficiently earlier than the effective U.S. filing date and any foreign priority date so that the particular month of publication is not in issue), pp. 135-151, Wiley-VCH Verlag GmbH & Co.. KGaA., Weinheim, Germany.
International Search Report and Written Opinion of the International Searching Authority, Search Report, Application No. PCT/EP2013/059980 issued by the European Patent Office, Rijswijk, Netherlands, dated of mailing Jul. 25, 2013.

* cited by examiner

*Primary Examiner* — Sikarl Witherspoon
(74) *Attorney, Agent, or Firm* — Peter B Scull; Hamilton, DeSanctis & Cha LLP

(57) ABSTRACT

A process for the preparation of methanol having the process a carbon oxides per-pass conversion equal to or higher than 65%, and a selectivity to methanol formation equal to or higher than 75% by submitting carbon dioxide, carbon monoxide or a mixture of carbon monoxide and carbon dioxide to a hydrogenation reaction using a specific metal compound and specific reaction conditions of temperature, pressure, space velocity and a specific range of molar ratio of hydrogen to carbon dioxide, of hydrogen to carbon monoxide, or of hydrogen to the mixture of carbon monoxide and carbon dioxide. It further relates to a process for converting the methanol obtained into dimethyl ether or into a mixture of $(C_2\text{-}C_8)$alkene and $(C_1\text{-}C_8)$alkane.

22 Claims, No Drawings

PROCESS FOR THE PREPARATION OF METHANOL AND METHANOL-DERIVED PRODUCTS FROM CARBON OXIDES

The present disclosure relates to a process for the preparation of methanol, dimethyl ether, alkanes and alkenes from carbon oxides.

BACKGROUND

Carbon dioxide is accumulating in the atmosphere and it is suggested to cause the so-called greenhouse effect. Therefore, the reduction of carbon dioxide from atmosphere and emission sources is of great interest to mitigate global warming. At the same time, the source of carbon atoms in carbon dioxide largely stems from burning fossil fuels, causing the loss of natural carbon resources on Earth. One attractive solution for both problems is to use this great amount of carbon dioxide for its transformation into valuable compounds and chemical fuels such as methanol and its transformation products. This will allow to reduce the carbon dioxide concentration in the atmosphere as well as to close the carbon cycle which has an open end at present.

Methanol is one of the primary chemicals for industries, and a promising alternative for oil and natural gas, with applications in energy storage, fuel cells and the preparation of a variety of bulk chemicals such as formaldehyde, dimethyl ether, ethylene, propylene, gasoline and acetic acid. The synthesis of methanol from hydrogen and carbon dioxide or from mixtures of hydrogen, carbon dioxide, and carbon monoxide (the so-called syngas) using a solid catalyst is still attracting much interest due to its economical and environmental relevance, thus making carbon dioxide a valuable and renewable carbon source rather than a cause of global warming.

Catalytic methanol synthesis from hydrogen and carbon dioxide or syngas is a well-known exothermic reaction with limited equilibrium, usually requiring moderately high temperature and pressure. The process of methanol synthesis can be summarized as follows:

Scheme 1

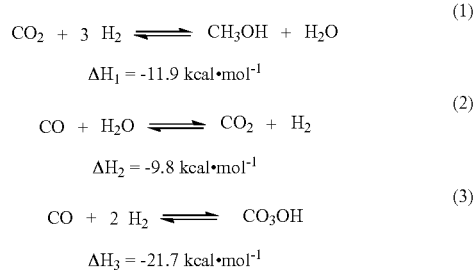

Methanol and carbon monoxide are produced competitively from carbon dioxide through methanol synthesis (equation (1)) and the reverse water gas shift reaction (equation (2) to the left). Therefore, it has been suggested that in order to increase the amount of methanol formed, a stoichiometric or superstoichiometric amount of hydrogen is required, i.e. a molar ratio of carbon dioxide to hydrogen equal to or higher than 1:3.

The first catalysts used in the commercial methanol synthesis were $ZnO/Cr_2O_3$, being the mixture enriched in ZnO. This process was operated at 350° C., and about 260 bar, by reacting hydrogen with a mixture of carbon dioxide and carbon monoxide (U.S. Pat. No. 1,569,775, and U.S. Pat. No. 1,558,559). This catalytic system suffers from deactivation and, in the process plant, a significant amount of the unreacted mixture of carbon oxides and hydrogen had to be recycled due to partial conversion of the oxides after one pass through the reactor.

Ipatieff and co-workers reported a process for methanol synthesis by reacting hydrogen with carbon dioxide, or with a mixture of carbon dioxide, and carbon monoxide, using a copper-alumina based catalyst with low GHSVs in the range of 900 to 1600 h$^{-1}$. The copper-alumina catalyst was prepared by a deposition precipitation method comprising the precipitation of copper carbonate within a suspension of alumina followed by calcination of the dried precipitate at 240° C. Although this process has high conversions of carbon oxides in one pass through the catalyst bed and it is selective to methanol formation, the amount of methanol obtained following this process per unit of time is too low for commercial application. (V. N. Ipatieff et al., "Synthesis of Methanol from Carbon Dioxide and Hydrogen over Copper-Alumina Catalysts. Mechanism of Reaction", *Journal of the American Chemical Society*, 1945, vol. 67, pp. 2168-2171).

Subsequently, other catalysts based on copper-zinc mixed oxides supported on or mixed with aluminum oxides were developed for methanol synthesis. These catalysts are usually prepared by co-precipitation of the corresponding metal oxides in aqueous medium, which enables to control the active surface of the catalyst and its copper content. The methanol production was typically carried out under moderate temperature (220-275° C.), and low-pressure (50-100 bar) conditions. Unfortunately, under the above-mentioned reaction conditions, a per-pass conversion of the process even using a high ratio H$_2$:rich syngas (H$_2$/CO=5) is limited to low total carbon oxides conversion. This low carbon oxides per-pass conversion has been attributed to the thermodynamic limitation of the highly exothermic reaction. Consequently, the recycling of unreacted carbon oxides is necessary to enhance their conversion, leading to a higher production cost associated with a more sophisticated process design.

The high exothermicity of the reaction is also well known to deactivate the catalyst of the reaction in the long term. In this area, Pontzen and co-workers reported a representative example of a process using a commercially available copper-zinc-aluminium oxide based catalyst for the synthesis of methanol by reacting hydrogen with carbon dioxide, at a temperature of 250° C. and a pressure of 70 bar, and a molar ratio of hydrogen to carbon dioxide of 3.1 to 1. This process has a high selectivity to methanol formation but the carbon oxides per-pass conversion proved to be low, since a loop reactor with product separation and internal recycle was required to achieve high overall conversions (F. Pontzen et al., "CO$_2$-based methanol and DME—Efficient technologies for industrial scale production" *Catalysis Today*, 2011, vol. 171, pp. 242-250).

Another copper-based catalyst has been disclosed with the purpose of improving per-pass methanol yields. A binary catalyst based on the combination of a homogeneous potassium formate catalyst and a solid copper-magnesia catalyst in alcohol solvents was used for methanol synthesis starting from syngas at low temperature (Tian-Sheng Zhao, et al. "A novel low-temperature methanol synthesis method from CO/H$_2$/CO$_2$ based on the synergistic effect between solid catalyst and homogeneous catalyst", *Catalysis Today*, 2010, vol. 149, pp. 98-104). Unfortunately, due to the use of a solvent and of a homogeneous catalyst, the methanol production at industrial scale is not easy to realize.

Alternatively, another methanol synthesis under modified reaction conditions, such as supercritical conditions, was performed with the purpose of improving per-pass methanol yields. A copper-zinc based catalyst (Cu/ZnO) was employed for methanol formation under supercritical conditions. The reaction conditions therein disclosed imply a temperature of 270° C., a pressure of 62 bar, and the addition of solvents, for instance n-hexane or 2-butanol. (Prasert Reubroycharoen, et al. "Methanol Synthesis in Inert or Catalytic Supercritical Fluid", *Fischer-Tropsch Synthesis, Catalysts and Catalysis, Studies in Surface Science and Catalysis*, 2007, vol. 163, pp. 367-378). Unfortunately, the continuous process for preparing methanol requires a large quantity of the solvent, and thus, the use of the above-mentioned conditions at industrial scale production of methanol is difficult to be implemented.

Additionally, the document US2010088951 describes a process for the synthesis of methanol from synthesis gas, namely a mixture of carbon monoxide and hydrogen with a ratio of hydrogen to carbon monoxide comprised from 0.5 to 1, under a pressure comprised from 35 to 200 bar, at a temperature of 275-300° C., at a space velocity comprised from 2000 to 4000 h$^{-1}$, and in the presence of a catalyst comprising copper, zinc and potassium.

Similarly, the document U.S. Pat. No. 4,477,594 describes a process for the synthesis of a mixture of methanol and aliphatic hydrocarbons from carbon monoxide and hydrogen in the presence of a catalyst comprising copper, aluminium, zinc, potassium and other metal oxides, under a pressure of 35-200 bar, at a temperature between 200 and 450° C. These processes produce methanol along with other alcohols and by-products with a low carbon oxide conversion, and a low selectivity to methanol formation, as well as a low productivity of methanol.

Therefore, from what is known it is derived that there is still the need of providing a more productive process for the preparation of methanol by reduction of carbon oxides with a high per-pass conversion, high selectivity, and without the deactivation of the catalyst used.

SUMMARY

Disclosed here is a more productive process for preparing methanol having both a high carbon oxides per-pass conversion, and a high selectivity to methanol formation with respect to the by-products formed in the reaction, i.e. carbon monoxide, dimethyl ether, methyl formate, olefins, and alkanes among others. The process is based on the selection of a specific molar ratio of hydrogen to carbon dioxide, the molar ratio of hydrogen to the mixture of carbon dioxide and carbon monoxide, or the molar ratio of hydrogen to carbon monoxide, temperature, pressure, and space velocity to carry out an enhanced hydrogenation of carbon oxides in the presence of a mixture comprising specific mixtures of Cu and/or Zn, in form of free metal or in form of metal oxides to yield methanol. Thus, the process hereof allows having a process for preparing methanol with a high carbon oxides per-pass conversion avoiding the need of recycling the unreacted carbon oxides, and without deactivation of the mixture (I), or alternatively the mixture (II), or alternatively the mixture (III) as defined below. The amount of methanol obtained following the process hereof is generally comprised of from 600 to 7700 mg of methanol per gram of the mixture (I), or alternatively of the mixture (II), or alternatively of the mixture (III) per hour. Disclosed also are processes for the preparation of methanol derived products, such as dimethyl ether (DME), alkenes and alkanes using the process for the preparation of methanol hereof.

Thus, the present subject matter relates to a process for the preparation of methanol, with a carbon oxides per-pass conversion equal to or higher than 65%, and selectivity to methanol formation equal to or higher than 75%, comprising reacting hydrogen with carbon dioxide, carbon monoxide or mixtures thereof; at a pressure equal to or higher than 200 bar; at a temperature comprised of from 230 to 320° C.; and at a space velocity comprised of from 5,000 to 200,000 h$^{-1}$ in the presence of a mixture (I) comprising $M_1$ and $M_2$, or alternatively, in the presence of a mixture (II) comprising $M_1$, $M_2$ and at least a compound of formula $A_nO_m$, or alternatively, in the presence of a mixture (III) comprising $M_1$ and at least a compound of formula $A_nO_m$, wherein: the molar ratio of hydrogen to carbon dioxide, the molar ratio of hydrogen to the mixture of carbon dioxide and carbon monoxide, or the molar ratio of hydrogen to carbon monoxide is equal to or higher than 3:1; $M_1$ is Cu, CuO, $Cu_2O$ or a mixture thereof; $M_2$ is Zn, ZnO or a mixture thereof; A is a cation selected from the group consisting of $Mg^{2+}$, $Al^{3+}$, $Si^{2+}$, $Si^{4+}$, $Ti^{3+}$, $Ti^{4+}$, $V^{2+}$, $V^{3+}$, $V^{4+}$, $V^{5+}$, $Cr^{2+}$, $Cr^{3+}$, $Cr^{6+}$, $Zr^{4+}$, $Mn^{2+}$, $Mn^{3+}$, $Mn^{4+}$, $Mn^{6+}$, $La^{3+}$, $Ce^{3+}$, $Ce^{4+}$, and $Th^{4+}$; and n is an integer selected from 1 to 3; m is an integer selected from 1 to 9; being the sum of positive charges of $A_n$ equal to the sum of negative charges of $O_m$.

DETAILED DESCRIPTION

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

In the context of this disclosure and claims, "molar ratio" refers to the number of moles of molecular hydrogen with respect to the number of moles of carbon dioxide, or it refers to the number of moles of molecular hydrogen with respect to the sum of the number of moles of carbon dioxide and the number of moles of carbon monoxide, or it refers to the number of moles of molecular hydrogen with respect to the number of moles of carbon monoxide needed to produce methanol or methanol-derived products.

In the context hereof, the term "weight ratio" refers to the amount, expressed in gram, of $M_2$ divided by the amount, expressed in grams of $M_1$.

The term "catalytically effective amount" refers to the fact that the amount of the mixture (I), the mixture (II), the mixture (III), and/or the compound (IV) is sufficient for the catalyzed reaction to take place. In some particular cases, especially for non-continuous or batch processes and short continuous experiments, a "catalytically effective amount" refers to the fact that the amount of the mixture (I), the mixture (II), the mixture (III), and/or the compound (IV) is much smaller than the stoichiometric amount of each of the carbon oxides.

The term "super-stoichiometric effective amount" refers to the fact that the amount of the mixture (I), the mixture (II), the mixture (III), and/or the compound (IV) is higher than one molar equivalent of each of the carbon oxides required for the reaction to take place.

The term "syngas", "synthetic gas" or "synthesis gas" refers to a gas mixture that contains varying amounts of hydrogen, carbon monoxide, and carbon dioxide. Syngas is usually prepared from fossil fuels, for instance gas, or oil, by steam reforming or through biomass gasification. The composition of the syngas varies according to the way it is prepared. Most commonly, syngas contains molecular hydrogen as the main component, and an amount of carbon monoxide higher than the amount of carbon dioxide. The content of carbon dioxide of syngas can be increased by the treatment of syngas with water according to the water gas shift reaction following methods known in the art.

The term "carbon oxides" refers either to carbon monoxide, carbon dioxide or mixtures of carbon monoxide and carbon dioxide.

The term "carbon oxides per-pass conversion" or "conversion" have the same meaning, and are used interchangeably. They refer to the amount of carbon oxides ($CO_2$ and/or $CO$) transformed into another chemical compound relative to the initial amount of carbon oxides. In the specific case of a continuous process, it refers to the amount of carbon oxides transformed into another chemical compound relative to the initial amount of carbon oxides after one pass into the reactor. Alternatively, in the specific case of a batch process, it refers to the amount of carbon oxides transformed into another chemical compound relative to the initial amount of carbon oxides at the end of the reaction. This term is used to describe transformations that lead to more "valuable" chemicals, such as for example the conversion of CO and/or $CO_2$ into methanol, ethers, alkanes or alkenes. In the context hereof, the conversion is expressed as a percentage and it can be calculated by dividing the number of moles of carbon containing products formed during the process by the number of moles of carbon oxides initially present.

The terms "selectivity to methanol formation" or "selectivity to dimethyl ether (DME) formation" or "selectivity to alkane formation" or "selectivity to alkene formation", expressed as a percentage, refer to the molar amount of produced methanol, or to the molar amount of produced DME, or to the molar amount of produced alkane or to the molar amount of produced alkene with respect to the total molar amount of carbon-containing products obtained in the reaction.

The terms "molecular hydrogen", "hydrogen" or "$H_2$" have the same meaning, and are used interchangeably.

The term "space velocity" refers to the quotient of the entering volumetric flow rate of the reactants divided by the reactor volume, and indicates the reactor volumes of feed that can be treated in a unit time. Space velocity can be expressed as SV=u0/V, where u0 represents the volumetric flow rate of the reactants entering the reactor (e.g. expressed in $m^3$ per second or $m^3$ per hour), and V represents the volume of the reactor itself (e.g. expressed in $m^3$). Special values for this measurement exist for liquids and gases, and for systems that use solid catalysts.

The terms "gas hourly space velocity" or "GHSV" have the same meaning and are used interchangeably. GHSV is the specific measurement of the space velocity for gases, and it can be expressed as the reactant gas flow rate divided by the reactor volume or as (volume of feed as gas at standard temperature and pressure per unit of time)/(volume of the reactor or its content of catalyst).

The term "in situ" refers to the operation or procedure that is performed in place. In the context of the present disclosure and claims, accordingly, a mixture (I), a mixture (II), a mixture (III), or a compound (IV) activated "in situ" means that those compounds are reduced in the same enclosure where later the catalytic process takes place.

The term "($C_2$-$C_8$)alkene" or "olefin" have the same meaning and are used interchangeably.

The term "alkene" refers to a branched or linear hydrocarbon which contains the number of carbon atoms specified in the description or claims, and that also contains at least one double bond. Examples include, among others, ethenyl, 1-propen-1-yl, 1-propen-2-yl, 3-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, and 1,3-butadien-2-yl.

The term "alkane" refers to a saturated, branched or linear hydrocarbon which contains the number of carbon atoms specified in the description or claims. Examples include methane, ethane, propane, isopropane, butane, isobutane, sec-butane, and tert-butane.

The term "alkyl" refers to a saturated, branched or linear alkyl chain which contains the number of carbon atoms specified in the description or claims. Examples include the group methyl, ethyl, propyl, isopropyl, butyl, isobutyl, sec-butyl, and tert-butyl.

The term "mixture enriched in" refers to a mixture that has more of one component than another. For example, in the case of a mixture of ($C_2$-$C_8$)alkene and ($C_1$-$C_8$)alkane enriched in ($C_1$-$C_8$)alkane, the amount of ($C_1$-$C_8$)alkane is higher than the amount of ($C_2$-$C_8$)alkene.

As mentioned above, the present developments refer to a process for the preparation of methanol with a carbon oxides per-pass conversion equal to or higher than 65%, and selectivity to methanol formation equal to or higher than 75% with respect to the rest of by-products, for instance carbon monoxide, ethers, alkanes, and olefins, at a high GHSV for high methanol productivity.

Following the processes known in the state of the art for the preparation of methanol from carbon dioxide, carbon monoxide or from mixtures of carbon monoxide and carbon dioxide, the need of recycling the unreacted reagents such as carbon dioxide, carbon monoxide and hydrogen, as well as the reactivation of the catalyst are required in order to have a viable and profitable process. Avoiding some of the above-mentioned recycling or activation steps is considered a technical contribution to the art, as it allows for the significant reduction of the equipment required to the process of production of methanol and a longer catalyst lifetime.

In comparison with the processes disclosed in the prior art, the processes hereof increase both the chemical yield of methanol and the carbon oxides per-pass conversion, thereby in such an amount that the recycling of the unreacted carbon oxides is no longer necessary. Additionally, the amount of methanol obtained following the processes hereof per gram of the mixture (I), or of the mixture (II), or of the mixture (III) per hour is higher than the amount of methanol produced for the processes of the state of the art. Without being bound to theory, it is believed that the specific conditions of reaction used herein allow for a subtle balance of the rates of the involved chemical equilibrium in such a way that the reversed water gas shift reaction (equation 2, Scheme 1) is slowed down with respect to the other involved equilibrium, thus allowing for high selectivity to methanol and conversion of carbon oxides. It is also believed that the specific conditions of reaction used herein allow forming a liquid phase shifting the thermodynamic equilibrium towards the formation of methanol. Thereby, the processes hereof allow obtaining methanol with high conversions and selectivities.

On the other hand, as it is shown in the stability test of mixture (IIA) (cf. Table 6), the mixture (II) is not deactivated by poisoning or decomposition under the reaction conditions being stable under such conditions for about 130 h. The mixture (II) is also stable even if the processes hereof are stopped, and the mixture (II) is exposed to the air. That means that the mixture (II) can be directly used, without a prior activation step in subsequent hydrogenation reactions.

It is advantageous because the process can be carried out in a continuous way by adding the starting materials at a constant flow rate, for instance hydrogen, and carbon dioxide; and using the same mixture (I), mixture (II), or mixture (III) present in the reaction mixture. Thus, in a preferred embodiment, the process hereof is a continuous process.

In an embodiment, the process for the preparation of methanol with a carbon oxides per-pass conversion equal to or higher than 65%, and selectivity to methanol formation equal to or higher than 75%, comprises reacting hydrogen with carbon dioxide, carbon monoxide or mixtures thereof; at a pressure equal to or higher than 200 bar; at a temperature comprised of from 230 to 320° C.; and at a space velocity comprised of from 5,000 to 150,000 $h^{-1}$ in the presence of a mixture (I) comprising $M_1$ and $M_2$, or alternatively, in the presence of a mixture (II) comprising $M_1$, $M_2$ and at least a compound of formula $A_nO_m$, or alternatively, in the presence of a mixture (III) comprising $M_1$ and at least a compound of formula $A_nO_m$, wherein: the molar ratio of hydrogen to carbon dioxide, the molar ratio of hydrogen to the mixture of carbon dioxide and carbon monoxide, or the molar ratio of hydrogen to carbon monoxide is equal to or higher than 3:1; $M_1$ is Cu, CuO, $Cu_2O$ or a mixture thereof; $M_2$ is Zn, ZnO or a mixture thereof; A is a cation selected from the group consisting of $Mg^{2+}$, $Al^{3+}$, $Si^{2+}$, $Si^{4+}$, $Ti^{3+}$, $Ti^{4+}$, $V^{2+}$, $V^{3+}$, $V^{4+}$, $V^{5+}$, $Cr^{2+}$, $Cr^{3+}$, $Cr^{6+}$, $Zr^{4+}$, $Mn^{2+}$, $Mn^{3+}$, $Mn^{4+}$, $Mn^{6+}$, $La^{3+}$, $Ce^{3+}$, $Ce^{4+}$, and $Th^{4+}$; and n is an integer selected from 1 to 3; m is an integer selected from 1 to 9; the sum of positive charges of $A_n$ being equal to the sum of negative charges of $O_m$.

In another embodiment, the process for the preparation of methanol with a carbon oxides per-pass conversion equal to or higher than 65%, and selectivity to methanol formation equal to or higher than 80%, comprises reacting hydrogen with carbon dioxide, carbon monoxide or mixtures thereof; at a pressure equal to or higher than 200 bar; at a temperature comprised of from 230 to 320° C.; and at a space velocity comprised of from 5,000 to 20,000 $h^{-1}$ in the presence of a mixture (I) comprising $M_1$ and $M_2$, or alternatively, in the presence of a mixture (II) comprising $M_1$, $M_2$ and at least a compound of formula $A_nO_m$, or alternatively, in the presence of a mixture (III) comprising $M_1$ and at least a compound of formula $A_nO_m$, wherein: the molar ratio of hydrogen to carbon dioxide, the molar ratio of hydrogen to the mixture of carbon dioxide and carbon monoxide, or the molar ratio of hydrogen to carbon monoxide is equal to or higher than 3:1; $M_1$ is Cu, CuO, $Cu_2O$ or a mixture thereof; $M_2$ is Zn, ZnO or a mixture thereof; A is a cation selected from the group consisting of $Mg^{2+}$, $Al^{3+}$, $Si^{2+}$, $Si^{4+}$, $Ti^{3+}$, $Ti^{4+}$, $V^{2+}$, $V^{3+}$, $V^{4+}$, $V^{5+}$, $Cr^{2+}$, $Cr^{3+}$, $Cr^{6+}$, $Zr^{4+}$, $Mn^{2+}$, $Mn^{3+}$, $Mn^{4+}$, $Mn^{6+}$, $La^{3+}$, $Ce^{3+}$, $Ce^{4+}$, and $Th^{4+}$; and n is an integer selected from 1 to 3; m is an integer selected from 1 to 9; the sum of positive charges of $A_n$ being equal to the sum of negative charges of $O_m$.

In another embodiment, in the process for preparing methanol the mixture (I), or alternatively the mixture (II), or alternatively the mixture (III) is obtainable by co-precipitation. The co-precipitation method for the preparation of heterogeneous catalyst is well known in the state of the art. The co-precipitation process mainly comprises the following steps: precipitation, aging, filtration, washing, drying, and calcination. The precipitation step comprises the simultaneous precipitation of the metal salts. During the precipitation, aging, and/or calcination step the basic properties of the catalyst are established. Therefore, catalyst performance can be significantly influenced by changing the precipitation, aging, washing, and/or calcination conditions. (Cf. K. P. de jong, "Synthesis of Solid catalyst", Wiley-VCH Verlag GmbH & Co. KGaA., 2009, Weinheim, Chapter. 7. Co-precipitation, pp. 135-151).

The term "obtainable" or "obtained" as used in the present disclosure and claims have the same meaning and are used interchangeable. In any case, the term "obtainable" includes the term "obtained".

In a preferred embodiment, the process for the preparation of methanol is carried out in the presence of the mixture (I) comprising $M_1$ and $M_2$, obtainable by a process comprising: (a) contacting CuX, and ZnY with a base to form a precipitate; (b) filtering, washing, and drying the precipitate obtained in step (a) to form a solid; and (c) calcining the solid obtained in step (b); or alternatively, the process for the preparation of methanol is carried out in the presence of the mixture (II) comprising $M_1$, $M_2$ and at least a compound of formula $A_nO_m$ obtainable by a process comprising: (a') contacting CuX, ZnY, and AZ with a base to form a precipitate; (b') filtering, washing, and drying the precipitate obtained in step (a') to form a solid; and (c') calcining the solid obtained in step (b'); or alternatively, the process for the preparation of methanol is carried out in the presence of the mixture (III) comprising $M_1$ and at least a compound of formula $A_nO_m$ obtainable by the process comprising: (a") contacting CuX and AZ with a base to form a precipitate; (b") filtering, washing, and drying the precipitate obtained in step (a") to form a solid; and (c") calcining the solid obtained in step (b"); wherein X, Y, and Z are each an anion independently selected from the group consisting of $NO_3^-$, $Cl^-$, $Br^-$, $F^-$, $I^-$, $CO_3^{2-}$, $HCO_3^-$, $SO_4^{2-}$, $CH_3COO^-$, $C_2O_4^{2-}$, $CN^-$ and tartrate.

In an embodiment of the invention, the co-precipitation process for preparing mixture (I), mixture (II), or mixture (III) further comprises an additional step after step (a), (a'), or (a") of aging the precipitate obtained in step (a). Preferably, the aging step is carried out for a time period comprised from 24 to 72 h.

In a preferred embodiment, X, Y and Z are each an anion independently selected from $NO_3^-$, $Cl^-$ and $CH_3COO^-$.

In a preferred embodiment, in the precipitation step (a), (a'), or (a") of the co-precipitation process for preparing mixture (I), mixture (II), or mixture (III) the base used is selected from the group consisting of alkaline, ammonium or alkaline-earth hydroxides; alkaline, ammonium or alkaline-earth carbonates; alkaline, ammonium or alkaline-earth bicarbonates; and alkaline citrate. Preferably, the base is selected from sodium carbonate, potassium carbonate, sodium hydroxide, ammonium bicarbonate and potassium hydroxide. Even more preferably, the base is potassium hydroxide.

In a preferred embodiment, in the precipitation step (a), (a'), or (a") of the co-precipitation process for preparing mixture (I), mixture (II), or mixture (III), X, Y, and Z are $NO_3^-$.

In a preferred embodiment, in the precipitation step (a), (a'), or (a") of the co-precipitation process for preparing mixture (I), mixture (II), or mixture (III), the base used is KOH, and X, Y, and Z are $NO_3^-$.

In a preferred embodiment, the precipitation step (a), (a'), or (a") of the co-precipitation process for preparing mixture (I), mixture (II), or mixture (III) is carried out at a temperature comprised from 60 to 95° C.; Preferably, the temperature is comprised from 70 to 90° C. More preferably, the temperature is about 80° C.

In a preferred embodiment, the precipitation step (a), (a'), or (a") of the co-precipitation process for preparing mixture (I), mixture (II), or mixture (III) is carried out at a pH comprised from 8 to 11; Preferably, the pH is comprised from 9.5 to 10.5.

In an embodiment hereof, the calcination step (c), (c'), or (c") of the co-precipitation process for preparing mixture (I), mixture (II), or mixture (III), is carried out at a temperature comprised from 250 to 500° C.; Preferably, the temperature is comprised from 350 to 450° C. More preferably, the temperature is about 400° C.

In an embodiment hereof, the mixture (I), the mixture (II), or the mixture (III) is only activated once, concretely before carrying out the first hydrogenation reaction. Therefore, in this embodiment the process further comprises a previous step of activating the mixture (I), the mixture (II), or the mixture (III). The mixture (I), the mixture (II), or the mixture (III) can be activated by the reduction of the corresponding Zn and/or Cu oxides in the presence of hydrogen. In a more preferred embodiment, the process further comprises a previous step of activating the mixture (I), the mixture (II), or the mixture (III) at a temperature comprised of from 250 to 400° C. during a time comprised of from 1 to 5 hours under hydrogen atmosphere.

In another embodiment hereof, when the content of hydrogen in the reaction mixture is higher than 69%, the process can be carried out without activation. In such a case, the metal oxides forming part of the mixture (I), the mixture (II), or the mixture (III) are totally or partially reduced in situ in the reaction mixture by the action of the hydrogen.

In an embodiment hereof, the process for the preparation of methanol is carried out in the presence of the mixture (I), or the mixture (II), or the mixture (III) obtainable by the co-precipitation process as defined above; wherein $M_1$ is comprised from 20 to 90% by weight; Preferably, $M_1$ is comprised from 25 to 70% by weight.

In an embodiment hereof, the process for the preparation of methanol is carried out in the presence of the mixture (II) obtainable by the co-precipitation process as defined above; wherein $M_1$ is comprised from 20 to 90% by weight and $A_nO_m$ is comprised from 4 to 50% by weight; Preferably, the process for the preparation of methanol is carried out in the presence of the mixture (II) wherein $M_1$ is comprised from to 75% by weight and $A_nO_m$ is comprised from 4 to 50% by weight.

Finally, the reaction conditions of the processes hereof facilitate the recycling of the unreacted hydrogen. Thus, in a preferred embodiment, the process as defined above further comprises an additional step of separating the unreacted hydrogen.

The process for recycling hydrogen can be carried out by flash evaporation. Preferably, the recycling of hydrogen is carried out by flash evaporation operated at high pressure. Flash evaporation is the operation in which a partial vapor is generated when a saturated liquid stream undergoes a reduction in pressure by passing through a throttling valve or other throttling devices. If the throttling valve or device is located at the entry into a pressure vessel so that the flash evaporation occurs within the vessel, then the vessel is often referred to as a flash drum.

When the process hereof is a continuous process, the unreacted hydrogen can be fed back through a recycle loop to the reactor wherein the process is carried out, or alternatively, to a subsequent reactor connected in series to the first reactor wherein the process is carried out.

Thus, in a preferred embodiment, the process for the reuse of hydrogen comprises: (a) separating the hydrogen from the product, preferably at high pressure; (b) introducing the hydrogen to another reactor connected in series with the first reactor; and (c) reacting the hydrogen with an additional amount of carbon oxides in the presence of a mixture (I), of a mixture (II), or of a mixture (III) in the second reactor. Several reactors can also be connected in series for reusing the unreacted hydrogen. The size of the reactors can decrease along the series because of the reduced hydrogen amount.

The processes hereof are carried out at high pressure. The use of high pressures advantageously allows for reducing the reactor size at the same production rate. It is advantageous because the cost of the process and the required energy for carrying out the process can be reduced. Additionally, the use of high pressure also allows for carrying out the process at lower flow rate of starting materials in the reactor, thereby decreasing the pressure-drops and increasing the contact time of the reactants with the catalysts.

Generally, the addition of carbon dioxide is carried out through a liquid pump, thus rendering the process safer, and easily handled.

The process for the preparation of methanol according to the disclosure and claims hereof can yield a carbon oxides per-pass conversion equal to or higher than the following percentages: 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. In addition, the process for the preparation of methanol hereof can yield a selectivity to methanol formation equal to or higher than the following percentages: 80%, 81%, 82%, 83%, 84%, 85%, 86%, 87%, 88%, 89%, 90%, 91%, 92%, 93%, 94%, 95%, 96%, 97%, 98%, and 99%.

In a preferred embodiment, the process according to the disclosure and claims hereof is carried out at a pressure comprised of from 200 to 1000 bar. In a preferred embodiment, the process is carried out at a pressure comprised of from 300 to 500 bar.

In a more preferred embodiment, the process is carried out at a pressure comprised of from 350 to 400 bar. Preferably, the process hereof is carried out at a pressure of about bar.

In another preferred embodiment, the process according to the disclosure and claims hereof is carried out at a temperature comprised of from 230 to 320° C. In a more preferred embodiment, the process is carried out at a temperature comprised of from to 300° C.; more preferably, at a temperature comprised of from 240 to 300° C.; much more preferably at a temperature comprised from 260 to 300° C. Preferably, the process hereof is carried out at a temperature of about 260° C.

In another preferred embodiment, the molar ratio of hydrogen to carbon dioxide, the molar ratio of hydrogen to the mixture of carbon dioxide and carbon monoxide, or the molar ratio of hydrogen to carbon monoxide is comprised of from 3:1 to 20:1. In a more preferred embodiment, the molar ratio of hydrogen to carbon dioxide, the molar ratio of hydrogen to the mixture of carbon dioxide and carbon monoxide, or the molar ratio of hydrogen to carbon monoxide is comprised of from 7:1 to 20:1. In a much more preferred embodiment, the molar ratio of hydrogen to carbon dioxide, the molar ratio of hydrogen to the mixture of carbon dioxide and carbon monoxide, or the molar ratio of hydrogen to carbon monoxide is comprised of from 8:1 to 20:1. In a still much more preferred embodiment, the molar ratio of hydrogen to carbon dioxide, the molar ratio of hydrogen to the mixture of carbon dioxide and carbon monoxide, or the molar ratio of hydrogen to carbon monoxide is comprised of from 10:1 to 20:1. Preferably, the molar ratio of hydrogen to carbon dioxide, the molar ratio of hydrogen to the mixture of carbon dioxide and carbon monoxide, or the molar ratio of hydrogen to carbon monoxide is 10:1.

In another preferred embodiment, the process according to the disclosure and claims hereof is carried out at a pressure comprised of from 200 to 1000 bar, and the molar ratio of hydrogen to carbon dioxide, the molar ratio of hydrogen to the mixture of carbon dioxide and carbon monoxide, or the molar ratio of hydrogen to carbon monoxide is comprised of from 3:1 to 20:1. In a preferred embodiment, the process is carried out at a pressure comprised of from 350 to 400 bar, and the molar ratio of hydrogen to carbon dioxide, the molar ratio of hydrogen to the mixture of carbon dioxide and carbon monoxide, or the molar ratio of hydrogen to carbon monoxide is comprised of from 3:1 to 20:1.

In a preferred embodiment, the process according to the disclosure and claims hereof is carried out at a space velocity comprised of from 5,000 to 150,000 h$^{-1}$. In a preferred embodiment, the space velocity is comprised of from 5,000 to 100,000 h$^{-1}$; more preferably, the space velocity is comprised of from 5,000 to 50,000 h$^{-1}$. In a much more preferred embodiment, the space velocity is comprised of from 5,000 to 20,000 h$^{-1}$. In a still more preferred embodiment, the process hereof is carried out at a space velocity comprised of from 8,000 to 15,000 h$^{-1}$. In a more preferred embodiment, the process hereof is carried out at a space velocity comprised of from 9,000 to 11,000 h$^{-1}$.

In a preferred embodiment, the process according to the disclosure and claims hereof comprises reacting hydrogen with carbon dioxide, carbon monoxide or their mixtures in the presence of the mixture (I), the mixture (II), or the mixture (III), wherein $M_1$ is selected from Cu, CuO and mixtures thereof and $M_2$ is selected from Zn, ZnO and mixtures thereof. Preferably, the mixture (I), the mixture (II), or the mixture (III) is commercially available.

In another preferred embodiment, the process hereof further comprises a previous step of preparing the mixture (I), the mixture (II), or the mixture (III) by co-precipitation. The process of co-precipitation comprises the steps as mentioned above.

In a preferred embodiment, the process hereof comprises reacting hydrogen with carbon dioxide, carbon monoxide or their mixtures in the presence of the mixture (I), or the mixture (II), or the mixture (III). In a more preferred embodiment, the process comprises reacting hydrogen with carbon dioxide, carbon monoxide or their mixtures in the presence of the mixture (I), or the mixture (II), or the mixture (III), wherein $M_1$ is Cu, and $M_2$ is ZnO. In another preferred embodiment, the process comprises reacting hydrogen with carbon dioxide, carbon monoxide or their mixtures in the presence of the mixture (I), or the mixture (II), or the mixture (III) wherein $M_1$ is CuO, and $M_2$ is ZnO.

Preferably, the process of the disclosure and claims hereof comprises reacting hydrogen with carbon dioxide, carbon monoxide or mixtures thereof in the presence of a mixture (II). In a more preferred embodiment, the process hereof is carried out reacting hydrogen with carbon dioxide, carbon monoxide or mixtures thereof in the presence of a mixture (II), wherein A is a cation selected from the group consisting of $Mg^{2+}$, $Al^{3+}$, $Si^{2+}$, $Si^{4+}$, $Zr^{4+}$, $La^{3+}$, $Ce^{3+}$, $Cr^{3+}$ and $Ce^{4+}$. In a much more preferred embodiment, in the mixture (II), A is $Mg^{2+}$ and/or $Al^{3+}$. In a still much more preferred embodiment, in the mixture (II), A is $Al^{3+}$, n is 2, and m is 3.

In a preferred embodiment, the process of the disclosure and claims hereof comprises reacting hydrogen with carbon dioxide, carbon monoxide or their mixtures in the presence of the mixture (I), the mixture (II), or the mixture (III), wherein $M_1$ is selected from Cu, CuO and mixture thereof; $M_2$ is selected from Zn, ZnO and mixture thereof; and A is selected from $Mg^{2+}$, $Al^{3+}$, and mixture thereof. In a preferred embodiment, the process hereof comprises reacting hydrogen with carbon dioxide, carbon monoxide or their mixtures in the presence of the mixture (II), or the mixture (III), wherein $M_1$ is CuO, $M_2$ is ZnO, and A is selected from $Mg^{2+}$, $Al^{3+}$, and mixture thereof.

In an embodiment hereof, the process for the preparation of methanol is carried out in the presence of the mixture (I), or the mixture (II), or the mixture (III) wherein $M_1$ is comprised from 20 to 90% by weight; Preferably, $M_1$ is comprised from 25 to 70% by weight. In another embodiment, the process for the preparation of methanol is carried out in the presence of the mixture (II) wherein $M_1$ is comprised from 20 to 90% by weight and $A_nO_m$ is comprised from 4 to 50% by weight. In a preferred embodiment, the process for the preparation of methanol is carried out in the presence of the mixture (II) wherein $M_1$ is comprised from 25 to 75% by weight and $A_nO_m$ is comprised from 4 to 50% by weight.

In a preferred embodiment, the mixture (II) is the mixture obtained after activation of the mixture (IIA) wherein the content of CuO is 29% by weight, the content of ZnO is 28% by weight, and the content of $Al_2O_3$ is 43% by weight. The mixture (IIA) is preferably used for the preparation of methanol from carbon dioxide, from carbon monoxide, or from a mixture of carbon dioxide and carbon monoxide.

In another preferred embodiment, the mixture (II) is the mixture obtained after activation of the mixture (IIB) wherein the content of CuO is 48% by weight, the content of ZnO is 47% by weight, and the content of $Al_2O_3$ is 5% by weight. The mixture (IIB) is preferably used for the preparation of a valuable product, such as dimethyl ether, from methanol, which has been firstly prepared from carbon dioxide, from carbon monoxide or from a mixture of carbon dioxide and carbon monoxide as it is mentioned below.

In another preferred embodiment, the mixture (II) is the mixture obtained after activation of the mixture (IIC) wherein the content of CuO is 63.5% by weight, the content of ZnO is 24.7% by weight, and the content of $Al_2O_3$ is 10.1% by weight. The mixture (IIC) further comprises MgO as a doping oxide, being the content of MgO of 1.3% by weight. The mixture (IIC) is preferably used for the preparation of methanol from carbon dioxide, from carbon monoxide, or from a mixture of carbon dioxide and carbon monoxide. Mixture (IIC) is commercially available with the name, Copper based methanol synthesis catalyst, from Alfa Aesar.

In another preferred embodiment the process of the disclosure and claims hereof comprises reacting hydrogen with carbon dioxide, carbon monoxide or mixtures thereof in the presence of a mixture (III). In a more preferred embodiment, the process hereof is carried out reacting hydrogen with carbon dioxide, carbon monoxide or mixtures thereof in the presence of a mixture (III), wherein A is a cation selected from the group consisting of $Mg^{2+}$, $Al^{3+}$, $Si^{2+}$, $Si^{4+}$, $Zr^{4+}$, $La^{3+}$, $Ce^{3+}$, $Cr^{3+}$ and $Ce^{4+}$. In a much more preferred embodiment, in the mixture (III), A is $Al^{3+}$, n is 2, and m is 3.

In a preferred embodiment, the mixture (III) is the mixture obtained after activation of the mixture (IIIA) wherein the content of CuO is 45% by weight, and the content of $Al_2O_3$ is 55% by weight.

In an embodiment hereof, the process for the preparation of methanol is carried out at a space velocity comprised of from 5,000 to 200,000 h$^{-1}$ in the presence of the mixture (IIA), or alternatively the mixture (IIB), or alternatively the mixture (IIC); preferably in the presence of mixture (IIC). In a preferred embodiment, the process for the preparation of methanol is carried out at a space velocity comprised of from 5,000 to 150,000 h$^{-1}$ in the presence of the mixture (IIA), or alternatively the mixture (IIB), or alternatively the mixture (IIC); preferably, in the presence of mixture (IIC). In a more preferred embodiment, the process for the preparation of methanol is carried out at a space velocity comprised of from 5,000 to 100,000 h$^{-1}$ in the presence of the mixture (IIA), or alternatively the mixture (IIB), or alternatively the mixture (IIC); preferably, in the presence of mixture (IIC).

In another embodiment hereof, the process for the preparation of methanol is carried out at a space velocity comprised of from 5,000 to 200,000 h$^{-1}$ in the presence of the mixture (IIIA). In a preferred embodiment, the process for the preparation of methanol is carried out at a space velocity comprised of from 5,000 to 150,000 h$^{-1}$ in the presence of the mixture (IIIA), In a more preferred embodiment, the process for the preparation of methanol is carried out at a space velocity comprised of from 5,000 to 100,000 h$^{-1}$ in the presence of the mixture (IIIA).

In an embodiment hereof, wherein when the process for the preparation of methanol is carried out in the presence of a mixture (I) comprising $M_1$ and $M_2$, or alternatively, in the presence of a mixture (II) comprising $M_1$, $M_2$ and at least a compound of formula $A_nO_m$, then the weight ratio of $M_2$ to $M_1$ is comprised from 0.1 to 2.1; Preferably, the weight ratio of $M_2$ to $M_1$ is comprised from 0.2 to 2.

The mixture (II) or the mixture (III) can be doped with additional metal oxides. The presence of this additional metal oxide increases the stability of the mixture (II), or of the mixture (III). In a preferred embodiment, the mixture (II) or the mixture (III) used herein further comprises additional metal oxides of formula $A'_{n'}O_{m'}$, wherein A' is a cation different from A, being A' selected from the group consisting of $Si^{4+}$, $Mg^{2+}$, $La^{3+}$, $Cr^{3+}$, $Ce^{4+}$, $Mn^{2+}$, $Mn^{3+}$, $Mn^{4+}$, $Mn^{6+}$, and $Zr^{4+}$; n' is an integer selected from 1 to 3; and m' is an integer selected from 1 to 9; the sum of positive charges of $A'_{n'}$ being equal to the sum of negative charges of $O_{m'}$. More preferably, A' is Mg, n' is 1 and m' is 1.

The process of the disclosure and claims can be carried out in a fixed bed reactor(s). A fixed bed reactor refers to a reactor in which solid granular mixture (I), mixture (II), or mixture (III) is packed on the fixed support. When the liquid or gas feed passes through the solid bed containing the mixture (I), the mixture (II), or the mixture (III) the chemical reactions takes place, and the mixture (I), the mixture (II), or the mixture (III) remains where it is with the feed flowing through it. It is advantageous because the process can be carried out in a continuous manner, allowing for a high productivity of methanol without requiring its separation from the mixture (I), the mixture (II), or the mixture (III). In a more preferred embodiment, the process hereof is carried out in more than one fixed bed reactor connected in parallel.

In another embodiment, the process hereof is carried out by reacting hydrogen with a mixture of carbon dioxide and carbon monoxide. Thus, when the process hereof is carried out by reacting hydrogen with a mixture of carbon monoxide and carbon dioxide, then the process further comprises a previous step of preparing a mixture of hydrogen with carbon monoxide and carbon dioxide. The above mentioned mixtures of hydrogen, carbon monoxide and carbon dioxide can be prepared from fossil fuels by steam reforming, or alternatively, from biomass by gasification.

The mixture thus obtained can be further submitted to the water gas shift reaction in order to increase its amount in carbon dioxide. Thus, when the process hereof is carried out by reacting hydrogen with a mixture of carbon monoxide and carbon dioxide, then the process further comprises previous steps of: (a) preparing a mixture of hydrogen with carbon monoxide and carbon dioxide, and (b) submitting the mixture obtained in step (a) to a water gas shift reaction. It is advantageous because the process yields a mixture of water and methanol that is enriched in methanol, allowing for an easier purification of methanol.

Without being bound to theory, it is believed that, when the process hereof is carried out by reacting hydrogen with a mixture of carbon monoxide and carbon dioxide, the carbon monoxide first reacts with the water produced in the formation of methanol from carbon dioxide to produce hydrogen and carbon dioxide. The carbon dioxide thus obtained with or without phase separation between reactants and products, is then converted to methanol and water in the specific conditions hereof. In case of phase separation, then the one-phase equilibrium conversion of $CO_2$ to methanol is overcome.

In another embodiment, the process is carried out by reacting hydrogen with carbon monoxide. Preferably, the process is carried out by reacting hydrogen with a mixture of carbon monoxide and water.

In a preferred embodiment, the process is carried out by reacting hydrogen with carbon dioxide. It is advantageous because the use of carbon dioxide as a carbon source in the preparation of valuable chemicals, such as methanol, is a long term search goal and allows for a non-dependency on fossil fuels for the methanol production, thereby closing the carbon cycle. Thus, a process for the production of methanol from carbon dioxide can be considered sustainable.

In a preferred embodiment, the process has a carbon oxides per-pass conversion equal to or higher than 90%, and selectivity to methanol formation equal to or higher than 80%, wherein: the process is carried out at a pressure comprised of from to 400 bar; at a temperature comprised of from 250 to 320° C.; and the molar ratio of hydrogen to carbon dioxide is comprised of from 8:1 to 20:1.

In a preferred embodiment, the process has a carbon oxides per-pass conversion equal to or higher than 90%, and selectivity to methanol formation equal to or higher than 80%, wherein: the process is carried out at a pressure comprised of from to 400 bar; at a temperature comprised of from 250 to 320° C.; at a space velocity comprised of from 8,000 to 15,000 h$^{-1}$; and the molar ratio of hydrogen to carbon dioxide is comprised of from 8:1 to 20:1.

In an alternative embodiment, the process has a carbon oxides per-pass conversion equal to or higher than 90%, and selectivity to methanol formation equal to or higher than 80%, wherein: the process is carried out in the presence of the mixture obtained after activation of the mixture (I), the mixture (II), or the mixture (III) at a pressure comprised of from 350 to 400 bar; at a temperature comprised of from 250 to 320° C.; at a space velocity comprised of from 8,000 to 15,000 h$^{-1}$; and the molar ratio of hydrogen to carbon dioxide is comprised of from 8:1 to 20:1; Preferably, in the presence of the mixture (IIA).

In a more preferred embodiment, the process has a carbon oxides per-pass conversion equal to or higher than 95%, and selectivity to methanol formation equal to or higher than 98%, wherein: the process is carried out at a pressure comprised of from to 400 bar; at a temperature comprised of from 250 to 300° C.; and the molar ratio of hydrogen to carbon dioxide is comprised of from 10:1 to 20:1.

In an alternative embodiment, the process has a carbon oxides per-pass conversion equal to or higher than 95%, and selectivity to methanol formation equal to or higher than 98%, wherein: the process is carried out in the presence of the mixture obtained after activation of the mixture (I), the mixture (II), or the mixture (III), at a pressure comprised of from 350 to 400 bar; at a temperature comprised of from 250 to 300° C.; and the molar ratio of hydrogen to carbon dioxide is comprised of from 10:1 to 20:1; Preferably, in the presence of the mixture (IIA).

In a more preferred embodiment, the process has a carbon oxides per-pass conversion equal to or higher than 95%, and selectivity to methanol formation equal to or higher than 98%, wherein: the process is carried out at a pressure comprised of from to 400 bar; at a temperature comprised of from 250 to 300° C.; at a space velocity comprised of from 8,000 to 15,000 $h^{-1}$; and the molar ratio of hydrogen to carbon dioxide is comprised of from 10:1 to 20:1.

In an alternative embodiment, the process has a carbon oxides per-pass conversion equal to or higher than 95%, and selectivity to methanol formation equal to or higher than 98%, wherein: the process is carried out in the presence of the mixture obtained after activation of the mixture (I), or the mixture (II), or the mixture (III), at a pressure comprised of from 350 to 400 bar; at a temperature comprised of from 250 to 300° C.; at a space velocity comprised of from 8,000 to 15,000 $h^{-1}$; and the molar ratio of hydrogen to carbon dioxide is comprised of from 10:1 to 20:1; Preferably, in the presence of the mixture (IIA).

In another preferred embodiment, the process has a carbon oxides per-pass conversion equal to or higher than 85%, and selectivity to methanol formation equal to or higher than 95%, wherein: the process is carried out in the presence of the mixture obtained after activation of the mixture (I), or the mixture (II), or the mixture (III), at a pressure comprised of from 350 to 400 bar; at a temperature comprised of from 250 to 300° C.; at a space velocity comprised of from 5,000 to 50,000 $h^{-1}$; and the molar ratio of hydrogen to carbon dioxide is comprised of from 10:1 to 20:1; Preferably, in the presence of the mixture (IIC).

The carbon dioxide used in the process can come from the atmosphere, or alternatively from a chemical process, for instance, combustion. In a preferred embodiment, when the process is carried out by reacting hydrogen with carbon dioxide, then the process further comprises a previous step of capturing carbon dioxide from atmosphere. It is advantageous because the carbon dioxide thus obtained can be stored prior to its use in methanol synthesis.

The hydrogen used in the process can be prepared from any process known in the state of the art. In particular, hydrogen may be prepared from water. The generation of hydrogen from water can be carried out by chemical, photochemical or electrochemical reactions known in the art. Thus, in another embodiment, the process further comprises a previous step of preparing hydrogen, preferably by electrolysis or through the water splitting reaction. The water splitting reaction allows for the generation of both hydrogen and oxygen from water molecules.

The process of the disclosure and claims yields methanol along with one water molecule per molecule of methanol formed, among other by-products. The water thus formed can be separated from the methanol by the methods known in the state of the art. Thus, in another embodiment, the process hereof further comprises an additional step of separating methanol from the reaction mixture, preferably by distillation.

When the process hereof is a continuous process, the amount of the mixture (I), or the mixture (II), or the mixture (III) varies depending on the number of cycles of the process. Thus, the amount of the mixture (I), or the mixture (II), or the mixture (III) can be comprised of from a catalytically effective amount to a super-stoichiometric effective amount. In a preferred embodiment, the amount of the mixture (I), or the mixture (II), or the mixture (III) is a catalytically effective amount.

The total amount of the mixture (I), or the mixture (II), or the mixture (III) used in the process hereof allows for higher production rates of methanol with respect to the process described in the state of the art, thus rendering the reaction more cost-effective, since, for equal amounts of produced methanol, the process hereof requires less amount of the mixture (I), or the mixture (II), or mixture (III) than the processes of the state of the art.

Processes for the conversion of methanol into other valuable compounds, such as for instance dimethyl ether (DME), alkanes, or alkenes are known from the state of the art.

DME is industrially important as the starting material in the production of methylating agent, dimethyl sulfide, and is also used in aerosols as a propellant gas. DME has also the potential to be used as a diesel or cooking fuel, as a refrigerant, or as chemical feedstock. DME is currently foreseen as a promising diesel fuel substituent or additive and thus has applications in automotive industry, electric power generation and domestic heating. DME is usually formed by dehydration of methanol in the presence of a compound resistant to the presence of water.

In an embodiment of the disclosure and claims, the process as defined above further comprises converting the methanol to dimethyl ether, with a carbon oxides per-pass conversion equal to or higher than 50%, and a selectivity to dimethyl ether formation equal to or higher than 70%, in the presence of a compound (IV) selected from the group consisting of alumina, silica-alumina, natural zeolites, synthetic aluminosilicate zeolite, and alumino-phospho-silicates.

This process comprises preparing methanol following the process as described herein and in the claims. Subsequently, the methanol thus obtained can be isolated or can be directly transformed in the presence of a compound (IV) to yield dimethyl ether. The transformation of methanol into dimethyl ether can be carried out in the same reactor as for methanol synthesis, or in another reactor, preferably connected in series. Methanol can be stored before dimethyl ether synthesis or can be used directly in dimethyl ether synthesis. The combination of temperature, pressure, space velocity and molar ratio of hydrogen to carbon dioxide, the molar ratio of hydrogen to the mixture of carbon monoxide and carbon dioxide, or the molar ratio of hydrogen to carbon monoxide used in the process hereof for methanol synthesis can be used in dimethyl ether synthesis from methanol. It is advantageous because methanol purification is not necessary for the preparation of dimethyl ether to be carried out with a carbon oxides per-pass conversion equal to or higher than 50%, and a selectivity to dimethyl ether formation equal to or higher than 70%. The progress of the reaction can be monitored by the common chromatographic techniques known in the art, such as for example gas chromatography (GC).

In a preferred embodiment, the process further comprises converting the methanol to dimethyl ether at a temperature comprised of from 230 to 320° C.; at a pressure comprised of from 350 to 400 bar; and the molar ratio of hydrogen to carbon dioxide, the molar ratio of hydrogen to the mixture of carbon dioxide and carbon monoxide, or the molar ratio of hydrogen to carbon monoxide is 10:1.

In a preferred embodiment, the process further comprises preparing dimethyl ether, by reacting hydrogen with carbon dioxide, carbon monoxide or mixtures thereof in the presence of the mixture (I), or alternatively the mixture (II), or alternatively the mixture (III), and in the presence of the compound (IV). It is advantageous because the preparation of methanol and the preparation of dimethyl ether are performed in the same reactor. Preferably, the process of the invention further comprises preparing dimethyl ether, by reacting hydrogen with carbon dioxide, carbon monoxide or mixtures thereof in the presence of the mixture (I), or alternatively the mixture (II), and in the presence of the compound (IV).

In a preferred embodiment, the process hereof further comprises converting the methanol to dimethyl ether, by separately adding a compound (IV). Thus, the mixture (I), the mixture (II), or the mixture (III) is firstly placed and packed into the closer side to the reactor inlet, and secondly, the compound (IV) is placed and packed into the same reactor but in the closer side to the reactor outlet being the bed of the mixture (I), the mixture (II), or the mixture (III) and the bed of the compound (IV) physically separated. In a more preferred embodiment, in the previous conversion of the methanol to dimethyl ether, the carbon oxides per-pass conversion is equal to or higher than 70%, and the selectivity of dimethyl ether formation is equal to or higher than 75%.

In another preferred embodiment, the process for the preparation of dimethyl ether as defined above that comprises separately adding a compound (IV), further comprises the previous step of pelletizing the mixture (I), the mixture (II), or the mixture (III); and the previous step of separately pelletizing the compound (IV). Then, mixture (I), mixture (II), or mixture (III), and compound (IV) are incorporated in the same reactor, being the mixture (I), the mixture (II), or the mixture (III), and compound (IV) physically separated.

In another preferred embodiment, the process further comprises converting the methanol to dimethyl ether, by carrying out the process as defined above for preparing methanol in the presence of a mixture of a mixture (I), a mixture (II), or a mixture (III), and a compound (IV). Thus, a physical mixture of the mixture (I), the mixture (II), or the mixture (III), and the compound (IV) is previously prepared, and the mixture thus formed is added to the reactor.

In a more preferred embodiment, in the previous conversion of the methanol to dimethyl ether, the carbon oxides per-pass conversion is equal to or higher than 50%, and the selectivity of dimethyl ether formation is equal to or higher than 70%.

In a more preferred embodiment, the process for the preparation of dimethyl ether as defined above by the addition of a mixture of the mixture (I), the mixture (II), or the mixture (III), and the compound (IV), further comprises the previous steps of preparing the mixture of mixture (I), mixture (II), or mixture (III), and compound (IV) which comprises:
(a) pelletizing the mixture (I); or alternatively the mixture (II); or alternatively the mixture (III);
(b) pelletizing the compound (IV); and
(c) physically mixing the mixture (I), the mixture (II), or the mixture (III) obtained in step (a), with the compound (IV) obtained in step (b).

Thus, the combination of the molar ratio of hydrogen to carbon dioxide, the molar ratio of hydrogen to the mixture of carbon monoxide and carbon dioxide, or the molar ratio of hydrogen to carbon monoxide, pressure, temperature, and space velocity defined above for the process of the invention allows having a high global carbon oxides per-pass conversion, a high selectivity to DME formation, and a higher amount of DME obtained per gram of the mixture (I), the mixture (II), or the mixture (III), and compound (IV) per unit of time.

Both above-mentioned alternative processes for the preparation of DME from methanol have a carbon oxides per-pass conversion equal to or higher than 50%, and a selectivity to DME formation equal to or higher than 70%. Consequently, the process of the invention for the preparation of DME can yield a carbon oxides per-pass conversion equal to or higher than the following percentages: 55%, 60%, 70%, 75%, 80%, 85%, 86%, 87%, 88%, 89%, 90%, 91%, 92%, 93%, 94%, 95%, 96%, 97%, 98%, and 99%. In addition, the process for the preparation of DME of the present invention can yield a selectivity to DME formation equal to or higher than the following percentages: 75%, 76% 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%.

In a particular embodiment, in the process for converting the above-obtained methanol into DME, the mixture (II) used for preparing methanol from carbon dioxide, or carbon monoxide, or a mixture of carbon dioxide and carbon monoxide is the mixture obtained after activation of the mixture (IIB).

In a particular embodiment, in the process for converting the above-obtained methanol into DME, the compound (IV) is selected from the group consisting of alumina and alumino-silicate zeolites. Preferably, the compound (IV) is a synthetic alumino-silicate zeolite. More preferably, the compound (IV) is a synthetic alumino-silicate zeolite selected from the group consisting of pentasil zeolite and a salt thereof, such as for example the crystalline alumino-silicate zeolite defined in claim 1 of the U.S. Pat. No. 3,702,886, having the X-Ray diffraction lines of Table 1 of the specification of U.S. Pat. No. 3,702,886:

TABLE 1

| Interplanar spacing d(A): | Relative intensity |
|---|---|
| 11.1 ± 0.2 | s. |
| 10.0 ± 0.2 | s. |
| 7.4 ± 0.15 | w. |
| 7.1 ± 0.15 | w. |
| 6.3 ± 0.1 | w. |
| 6.04 } ±0.1<br>5.97 | w. |
| 5.56 ± 0.1 | w. |
| 5.01 ± 0.1 | w. |
| 4.60 ± 0.08 | w. |
| 4.25 ± 0.08 | w. |
| 3.85 ± 0.07 | v.s. |
| 3.71 ± 0.05 | s. |
| 3.04 ± 0.03 | w. |
| 2.99 ± 0.02 | w. |
| 2.94 ± 0.02 | w. |

The zeolite defined in claim 1 of U.S. Pat. No. 3,702,886 is commercially available with the name ZSM-5 (IVA) or its ammonium salt ($NH_4$—ZSM-5).

In a preferred embodiment, in the process for converting the above-obtained methanol into DME, the mixture (II) is the mixture obtained after activation of mixture (IIB), and the compound (IV) is the compound (IVA).

When the process hereof is a continuous process, the amount of the compound (IV) varies depending on the number of cycles of the process. Thus, the amount of the compound (IV) can be comprised of from a catalytically effective amount to a super-stoichiometric effective amount. In a preferred embodiment, the amount of the compound (IV) is a catalytically effective amount.

The performance of the compound (IV) used in the process hereof is resistant to the presence of water. It is advantageous because the process for the preparation of DME defined above can be carried out in a unique reactor whereby carbon dioxide, carbon monoxide, or a mixture of carbon monoxide and carbon dioxide with hydrogen yields DME following one of the above-mentioned alternatives.

($C_1$-$C_8$)alkane are commonly used for heating and cooking purposes as well as for the generation of electricity.

Alkenes (olefins), such as ($C_2$-$C_8$)alkene, are industrially important as starting materials in the production of many chemical compounds, such as polymers among others.

In an embodiment hereof, the process as defined above further comprises converting the methanol to a mixture of ($C_2$-$C_8$)alkene and ($C_1$-$C_8$)alkane, in the presence of a compound (IV) selected from the group consisting of synthetic alumino-silicate zeolite, and alumino-phospho-silicates at a temperature comprised of from higher than 320 to 600° C.; and at a pressure comprised of from 1 to 400 bar.

This process comprises preparing methanol following the process hereof. The transformation of methanol into a mixture of ($C_2$-$C_8$)alkene and ($C_1$-$C_8$)alkane can be carried out in the same reactor as for methanol synthesis, or alternatively in another reactor, preferably connected in series. Methanol can be stored before the synthesis of the mixture of ($C_2$-$C_8$)alkene and ($C_1$-$C_8$)alkane or can be used directly in the synthesis of the mixture of ($C_2$-$C_8$)alkene and ($C_1$-$C_8$)alkane. Subsequently, the methanol thus obtained can be isolated or can be directly transformed in the presence of the compound (IV) selected from the group consisting of synthetic alumino-silicate zeolite, and alumino-phospho-silicates to yield a mixture of ($C_2$-$C_8$)alkene and ($C_1$-$C_8$)alkane. It is advantageous because methanol purification is not necessary for the preparation of a mixture of ($C_2$-$C_8$)alkene and ($C_1$-$C_8$)alkane from hydrogen and carbon dioxide, or from hydrogen and a mixture of carbon monoxide and carbon dioxide, or from hydrogen and carbon monoxide. The progress of the reaction can be monitored by the common chromatographic techniques known in the art, such as for example gas chromatography (GC).

In a preferred embodiment, the process further comprises converting the methanol to a mixture of ($C_2$-$C_8$)alkene and ($C_1$-$C_8$)alkane, by contacting separately the methanol with the compound (IV) selected from the group consisting of synthetic alumino-silicate zeolite, and alumino-phospho-silicates. Thus, the mixture (I), the mixture (II), or the mixture (III) is added to a first reactor, and the compound (IV) is added to a second reactor connected in series. The methanol formed in the first reactor is introduced in the second reactor where the transformation of methanol to the mixture of ($C_2$-$C_8$) alkene and ($C_1$-$C_8$)alkane is carried out. It is advantageous because this process allows for using different conditions of temperature, pressure and space velocity for the preparation of a mixture of ($C_2$-$C_8$)alkene and ($C_1$-$C_8$)alkane from methanol than the ones used in the process of the preparation of methanol of the present invention as defined herein, thereby allowing for fine-tuning of the product selectivity and yield. Preferably, the mixture (I), the mixture (II), or the mixture (III) is added to a first reactor, and the compound (IV) is added to a second reactor connected in series.

In a preferred embodiment, the process for the preparation of a mixture of ($C_2$-$C_8$)alkene and ($C_1$-$C_8$)alkane as defined above further comprises the previous step of pelletizing the mixture (I), the mixture (II), or the mixture (III); and the previous step of separately pelletizing the compound (IV). Then, mixture (I), mixture (II), or mixture (III), and compound (IV) are incorporated in the corresponding reactor.

In another preferred embodiment, the process further comprises converting the methanol to a mixture of ($C_2$-$C_8$)alkene and ($C_1$-$C_8$)alkane, by carrying out the process as defined above for preparing methanol in the presence of a mixture of a mixture (I), a mixture (II), or a mixture (III), and the compound (IV) selected from the group consisting of synthetic alumino-silicate zeolite, and alumino-phospho-silicates. Thus, a physical mixture of the mixture (I), the mixture (II), or the mixture (III), and the compound (IV) is previously prepared, and the mixture thus formed is added to the reactor. It is advantageous because the preparation of the mixture of ($C_2$-$C_8$)alkene and ($C_1$-$C_8$)alkane can be carried out in a unique reactor. Preferably, the process hereof further comprises converting the methanol to a mixture of ($C_2$-$C_8$)alkene and ($C_1$-$C_8$)alkane, by carrying out the process as defined above for preparing methanol in the presence of a mixture of a mixture (I), or a mixture (II), and a compound (IV).

In another preferred embodiment, when the process hereof further comprises converting the methanol to a mixture of ($C_2$-$C_8$)alkene and ($C_1$-$C_8$)alkane as defined above by the addition of a physical mixture of the mixture (I), the mixture (II), or the mixture (III), and the compound (IV), then the process further comprises the previous steps of preparing the mixture of mixture (I), mixture (II), or mixture (III), and compound (IV) which comprise:

(d) pelletizing the mixture (I); or alternatively the mixture (II); or alternatively the mixture (III);
(e) pelletizing the compound (IV); and
(f) physically mixing the mixture (I), the mixture (II), or the mixture (III) obtained in step (a), with the compound (IV) obtained in step (b).

In a preferred embodiment, the process as defined herein comprises converting the methanol to a mixture of ($C_2$-$C_8$) alkene and ($C_1$-$C_8$)alkane wherein the ($C_2$-$C_8$)alkene is selected from the group consisting of ethylene, propylene, and butene; and the ($C_1$-$C_8$)alkane is selected from the group consisting of methane, ethane, propane, butane, and isobutane.

The percentage of ($C_2$-$C_8$)alkene and ($C_1$-$C_8$)alkane in the resulting mixture can vary depending on the reaction conditions.

When the process for transforming the methanol obtained following the process hereof is carried out at a pressure comprised of from 200 to 400 bar, then the mixture of ($C_2$-$C_8$) alkene and ($C_1$-$C_8$)alkane is a mixture enriched in ($C_1$-$C_8$) alkane. Thus, it is advantageous because the preparation of a mixture of ($C_2$-$C_8$)alkene and ($C_1$-$C_8$)alkane enriched in ($C_1$-$C_8$)alkane can be carried out in a unique reactor, or in a multi-reactor process whereby carbon oxides yield ($C_2$-$C_8$) alkene and ($C_1$-$C_8$)alkane following one of the above-mentioned alternatives.

When the process for transforming the methanol obtained following the process hereof is carried out at a pressure comprised of from 1 to 10 bar, then the mixture of ($C_2$-$C_8$)alkene and ($C_1$-$C_8$)alkane is a mixture enriched in ($C_2$-$C_8$)alkene. Thus, the preparation of a mixture of ($C_2$-$C_8$)alkene and ($C_1$-$C_8$)alkane enriched in ($C_1$-$C_8$)alkane is carried out in a multi-reactor process defined above.

In a particular embodiment, in the process for converting the above-obtained methanol into the mixture of ($C_2$-$C_8$) alkene and ($C_1$-$C_8$)alkane, the mixture (II) used for preparing methanol is the mixture (IIA).

In a particular embodiment, in the process for converting the above-obtained methanol into the mixture of ($C_2$-$C_8$) alkene and ($C_1$-$C_8$)alkane, the compound (IV) is a synthetic alumino-silicate zeolite. Preferably, the compound (IV) is a synthetic alumino-silicate zeolite selected from the group consisting of pentasil zeolite and a salt thereof, such as for example the compound ZSM-5 (IVA) as defined above and its ammonium salt ($NH_4$—ZSM-5).

In another particular embodiment, the compound (IV) is an alumino-phospho-sillicate such as for example the crystalline alumino-phospho-sillicate defined in Example 38 of the U.S.

Pat. No. 4,440,871, having the X-Ray diffraction lines of Table XII of the specification of U.S. Pat. No. 4,440,871:

TABLE XII

| 2θ | d | 100 × I/I₀ |
|---|---|---|
| 9.45-9.65 | 9.36-9.17 | 81-100 |
| 12.8-13.05 | 6.92-6.78 | 8-20 |
| 13.95-14.2 | 6.35-6.24 | 8-23 |
| 16.0-16.2 | 5.54-5.47 | 25-54 |
| 17.85-18.15 | 4.97-4.89 | 11-76 |
| 19.0 | 4.67 | 0-2 |
| 20.55-20.9 | 4.32-4.25 | 44-100 |
| 22.05-22.5 | 4.03-3.95 | 0-5 |
| 23.0-23.15 | 3.87-3.84 | 2-10 |
| 24.95-25.4 | 3.57-3.51 | 12-87 |
| 25.8-26.0 | 3.45-3.43 | 14-26 |
| 27.5-27.7 | 3.243-3.220 | 1-4 |
| 28.05-28.4 | 3.181-3.143 | 1-12 |
| 29.2-29.6 | 3.058-3.018 | 3-9 |
| 30.5-30.7 | 2.931-2.912 | 19-75 |
| 31.05-31.4 | 2.880-2.849 | 15-28 |
| 32.2-32.4 | 2.780-2.763 | 1-5 |
| 33.4-33.85 | 2.683-2.648 | 0-6 |
| 34.35-34.65 | 2.611-2.589 | 4-15 |
| 36.0-36.5 | 2.495-2.462 | 2-11 |
| 38.8-38.9 | 2.321-2.315 | 0-2 |
| 39.6-39.7 | 2.276-2.270 | 2-4 |
| 43.1-43.5 | 2.099-2.080 | 3-6 |
| 47.4-47.7 | 1.918-1.907 | 2-6 |
| 48.8-49.2 | 1.866-1.852 | 4-7 |
| 49.9-50.45 | 1.828-1.809 | 0-2 |
| 50.65-51.3 | 1.802-1.781 | 1-8 |
| 53.0-53.25 | 1.728-1.720 | 2-7 |
| 54.25-54.7 | 1.691-1.678 | 0-4 |
| 55.7-55.9 | 1.650-1.645 | 2-5 |

The alumino-phospho-sillicate defined in Example 38 of the U.S. Pat. No. 4,440,871 is commercially available with the name SAPO-34 (IVB) or its salts.

In a preferred embodiment, in the process for converting the above-obtained methanol into the mixture of ($C_2$-$C_8$) alkene and ($C_1$-$C_8$)alkane, the mixture (II) is the mixture obtained after activation of the mixture (IIA), and the compound (IV) is the compound (IVA).

When the process hereof is a continuous process, the amount of the compound (IV) varies depending on the number of cycles of the process. Thus, the amount of the compound (IV) can be comprised of from a catalytically effective amount to a super-stoichiometric effective amount. In a preferred embodiment, the amount of the compound (IV) is a catalytically effective amount.

The compound (IV) used in the process hereof is stable to the presence of water for the preparation of methanol as defined above. It is advantageous because the process for the preparation of the mixture of ($C_2$-$C_8$)alkene and ($C_1$-$C_8$)alkane defined above can be carried out in a unique reactor or without previous purification of methanol.

Throughout the description and claims the word "comprises" and variations of the word, are not intended to exclude other technical features, additives, components or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

The following abbreviations are used in the below examples:
MeOH: methanol
MF: methylformate
DME: dimethyl ether
Process for the Preparation of the Mixture IIA CuO/ZnO/$Al_2O_3$.

Aqueous solutions of copper nitrate hexahydrate (0.2 M), zinc nitrate hexahydrate (0.2 M), and aluminium nitrate nonahydrate (0.2 M) with potassium hydroxide (0.5 M) were added together to a round bottom flask to precipitate the corresponding hydroxides (co-precipitation method). During the precipitation, the round bottom flask was heated at 80° C. under constant stirring, and the pH of the precipitate was maintained between 9.5-10.5. The precipitate was aged for two days, and after that time the precipitate was filtered, and washed with distilled water until the pH reached a value of 7.5. Then, the precipitate was dried in an oven at 100° C. overnight, crushed, and calcined in air in a muffle furnace at 400° C. for 4 h to yield CuO/ZnO/$Al_2O_3$ (IIA). CuO/ZnO/$Al_2O_3$ (IIA) was determined by ICP elemental analysis: 27.8 wt % CuO, 26.5 wt % ZnO, and 45.7% $Al_2O_3$. The BET surface area of the mixture (IIA) was 125 $m^2$/g.

Process for the Preparation of the Mixture (IIIA) CuO/$Al_2O_3$.

The process for preparing the mixture (IIIA) comprises following the process described above by the preparation of mixture (IIA) using as starting materials aqueous solutions of copper nitrate hexahydrate, aluminium nitrate nonahydrate, and potassium hydroxide. The composition of Cu/$Al_2O_3$ catalyst was determined by ICP elemental analysis: 43.3 wt % CuO and 56.7 wt % $Al_2O_3$. The BET surface area of the mixture (IIIA) was 168 $m^2$/g.

Process for the Preparation of Methanol from Hydrogen and Carbon Dioxide

Examples 1-23

General Consideration

The tubular reactor has an internal diameter of 1.74 mm, an outside diameter of 3.24 mm, and the bed length is about 10 cm). The pressure in the reactor was regulated by an automatic back-pressure regulator (Jasco, BP 2080 plus). Liquid $CO_2$ syringe pump (Isco Teledyne 260D) was used to feed liquefied $CO_2$. A high pressure thermal mass flow controller (Bronkhorst) was used to maintain the constant flow of $H_2$/Ar (90/10 vol %) mixture. $H_2$ compressor (Haskel AG75) operated by compressed air with a long metal tube functioning as reservoir for compressed $H_2$, and two pressure regulators connected in series (GO regulator PR57 and TESCOM 44-1100) to remove the pressure fluctuations, installed before the $H_2$ mass flow controller. The effluent stream was analyzed by on-line GC instrument (Bruker 450) equipped with a Porapak Q+ Mol sieve column with TCD detector for analysis of gaseous products, and a CP wax 52 CB capillary column with FID detector for analysis of methanol and other oxygenates. The line from the reactor to GC was heated to 150° C. to avoid condensation of products.

Procedure
A) General Procedure for the Activation of the Mixture (IIA) or the Mixture (IIIA)

The mixture (IIA) or the mixture (IIIA) was first pelletized and sieved to a size of 100-300 μm. 170 mg of the mixture (IIA) or of the mixture (IIIA) were loaded in a tubular reactor and reduced in the stream of Argon (10 vol %) and $H_2$ (90 vol %) at 330° C. for 2 hours at atmospheric pressure. After the pre-reduction, the reactor was cooled down to room temperature.

B) Hydrogenation of Carbon Dioxide

The reaction mixture of hydrogen and $CO_2$ was then introduced into the reactor mixture resulting from step (A) at the total flow rate of 30 Nml/min at GHSV of ca. 10471 $h^{-1}$. The pressure and temperature were regulated to be maintained in the reactor at the below-described values shown in Table 1. Then, the composition of the effluent stream was analyzed by gas chromatography.

C) Results

The reaction conditions of pressure, temperature, and the molar ratio of hydrogen to carbon dioxide, as well as the carbon oxides per-pass conversion, and the amount of methanol and its selectivity in the effluent stream are shown in Table 1.

Values of mmol of produced methanol per gram of the mixture (II), or per gram of the mixture (III), per hour are shown in Table 2.

TABLE 1

| Exp. No | $H_2/CO_2$ ratio[1] | T (° C.) | P (bar) | $CO_2$ conv. (%). | Selectivity (mol %) | | | | |
|---|---|---|---|---|---|---|---|---|---|
| | | | | | MeOH | CO | $CH_4$ | MF | DME |
| 1[2] | 3.3:1 | 170 | 100 | 1.3 | 77.8 | 22.3 | 0.0 | 0.0 | 0.0 |
| 2[2] | 3.3:1 | 200 | 100 | 5.8 | 64.7 | 35.3 | 0.0 | 0.0 | 0.0 |
| 3[2] | 3.3:1 | 230 | 100 | 9.3 | 22.6 | 77.4 | 0.0 | 0.0 | 0.0 |
| 4[2] | 3.3:1 | 260 | 100 | 16.4 | 9.2 | 90.1 | 0.0 | 0.0 | 0.7 |
| 5[2] | 3.3:1 | 280 | 100 | 28.0 | 6.1 | 93.4 | 0.0 | 0.0 | 0.5 |
| 6[2] | 10:1 | 260 | 200 | 66.62 | 83.24 | 16.37 | 0.00 | 0.00 | 0.39 |
| 7[2] | 10:1 | 280 | 200 | 78.72 | 87.61 | 11.94 | 0.00 | 0.00 | 0.45 |
| 8[2] | 10:1 | 300 | 200 | 72.34 | 80.96 | 18.27 | 0.38 | 0.00 | 0.38 |
| 9[2] | 10:1 | 230 | 360 | 78.91 | 89.90 | 8.95 | 1.05 | 0.00 | 0.10 |
| 10[2] | 10:1 | 260 | 360 | 95.36 | 98.29 | 1.42 | 0.28 | 0.00 | 0.00 |
| 11[2] | 7:1 | 260 | 360 | 75.95 | 85.55 | 13.60 | 0.18 | 0.00 | 0.67 |
| 12[2] | 12:1 | 260 | 360 | 96.21 | 98.83 | 1.10 | 0.07 | 0.00 | 0.00 |
| 13[2] | 14:1 | 260 | 360 | 95.98 | 99.12 | 0.83 | 0.05 | 0.00 | 0.00 |
| 14[2] | 16:1 | 260 | 360 | 96.49 | 99.13 | 0.87 | 0.00 | 0.00 | 0.00 |
| 15[2] | 18:1 | 260 | 360 | 96.91 | 99.33 | 0.67 | 0.00 | 0.00 | 0.00 |
| 16[2] | 20:1 | 260 | 360 | 96.52 | 99.23 | 0.73 | 0.05 | 0.00 | 0.00 |
| 17[2] | 1.1:1 | 280 | 360 | 27.2 | 60.5 | 39.0 | 0.0 | 0.2 | 0.3 |
| 18[2] | 3.6:1 | 280 | 360 | 69.8 | 84.6 | 14.4 | 0.7 | 0.1 | 0.3 |
| 19[2] | 5.8:1 | 280 | 360 | 87.3 | 89.5 | 8.9 | 1.2 | 0.0 | 0.4 |
| 20[2] | 7.8:1 | 280 | 360 | 90.9 | 92.6 | 5.9 | 1.1 | 0.0 | 0.4 |
| 21[2] | 10:1 | 280 | 360 | 93.34 | 91.71 | 7.97 | 0.32 | 0.0 | 0.0 |
| 22[2] | 10:1 | 300 | 360 | 91.36 | 84.25 | 12.82 | 1.12 | 0.0 | 1.80 |
| 23[3] | 10:1 | 280 | 360 | 82.62 | 92.03 | 6.09 | 0.79 | 0.00 | 1.09 |

[1]Feed mixtures of $H_2/CO_2$ with the molar ratio described in Table 1 were obtained by varying the $CO_2$ and $H_2$ set points
[2]The mixture (IIA) was used in step A.
[3]The mixture (IIIA) was used in step A.

TABLE 2

| | (mmol/g-cat · h) | | | | |
|---|---|---|---|---|---|
| Exp. No | MeOH | CO | $CH_4$ | MF | DME |
| 1 | 0.98 | 0.28 | 0.00 | 0.00 | 0.00 |
| 2 | 3.55 | 1.92 | 0.00 | 0.00 | 0.00 |
| 3 | 1.92 | 6.84 | 0.00 | 0.00 | 0.00 |
| 4 | 1.43 | 13.95 | 0.00 | 0.00 | 0.11 |
| 5 | 1.61 | 24.70 | 0.00 | 0.00 | 0.14 |
| 6 | 20.53 | 4.04 | 0.00 | 0.00 | 0.10 |
| 7 | 28.11 | 3.83 | 0.00 | 0.00 | 0.14 |
| 8 | 21.89 | 4.94 | 0.10 | 0.00 | 0.10 |
| 9 | 27.70 | 2.76 | 0.32 | 0.00 | 0.03 |
| 10 | 36.61 | 0.53 | 0.11 | 0.00 | 0.00 |
| 11 | 34.83 | 5.61 | 0.07 | 0.00 | 0.27 |
| 12 | 31.33 | 0.35 | 0.02 | 0.00 | 0.00 |
| 13 | 27.25 | 0.23 | 0.01 | 0.00 | 0.00 |

TABLE 2-continued

| | (mmol/g-cat · h) | | | | |
|---|---|---|---|---|---|
| Exp. No | MeOH | CO | $CH_4$ | MF | DME |
| 14 | 24.13 | 0.21 | 0.00 | 0.00 | 0.00 |
| 15 | 21.71 | 0.15 | 0.00 | 0.00 | 0.00 |
| 16 | 19.52 | 0.14 | 0.01 | 0.00 | 0.00 |
| 17 | 6.61 | 0.53 | 0.11 | 0.00 | 0.00 |
| 22 | 30.06 | 4.58 | 0.40 | 0.00 | 0.64 |
| 23 | 29.78 | 1.88 | 0.25 | 0.00 | 0.35 |

Processes of comparative Example 1-5 were carried out at a pressure of 100 bar and at a temperature comprised of from 170 to 280° C. The pressure of the process was outside the claimed range.

The process of comparative Example 17 was carried out at a molar ratio of hydrogen to carbon dioxide of 1.1:1 that is outside the claimed range.

Processes of Examples 6-16, and 18-23 were carried out at a pressure, temperature, and molar ratio of hydrogen to carbon dioxide in the claimed range.

The results in Table 1, and Table 2 showed that the process of the invention (Examples 6-16, and 18-23) allows obtaining methanol with both a high carbon oxides per-pass conversion, high selectivity to methanol formation, and with an amount of methanol per mg of mixture (II), or of mixture (III) per hour higher than the ones described in the state of the art.

Nevertheless, processes of the comparative Examples 1-5, and 17 that were outside the claimed range gave rise to a lower carbon oxides per-pass conversion, and lower selectivity to methanol formation.

Thus, the Examples illustrate the fact that the combination of the four technical features, that is a molar ratio of hydrogen to carbon dioxide equal to or higher than 3:1; a pressure comprised equal to or higher than 200 bar; a temperature comprised of from to 320° C.; and a space velocity comprised of from 5,000 to 20,000 $h^{-1}$ in the presence of a mixture (II), or a mixture (III) results in a process for preparing methanol with a carbon oxides per-pass conversion equal to or higher than 65%, and a selectivity to methanol formation equal to or higher than 75%.

Process for the Preparation of Dimethyl Ether

Examples 24-43

Procedure A

Physical Mixture of the Mixture (II), and the Compound (IVA) H-ZSM-5

Example 24-38

The compound (IVA) was prepared by the thermal treatment of ammonium ZSM-5 at 500° C. for 4 hours. Prior to the mixing, the mixture (II) and the compound (IV) were each pelletized, crushed, and sieved in a size of 100-300 μm separately. Then, the physical mixture of the mixture (II), and compound (IVA) thus obtained were added to the same tubular reactor.

The reaction mixture of hydrogen and $CO_2$ was then introduced into the tubular reactor at the total flow rate of 30 Nml/min at GHSV of ca. 10471 $h^{-1}$.

The reaction conditions of pressure, temperature, and molar ratio of hydrogen to carbon dioxide, as well as the carbon oxides per-pass conversion, and the amount of dimethyl ether obtained and its selectivity in the effluent stream are shown in Table 3.

Values of mmol of produced dimethyl ether per gram of the mixture (II) per hour are shown in Table 4.

Procedure B

Separate Addition of $CuO/ZnO/Al_2O_3$ (II) and H-ZSM-5 (IVA)

Example 39-43

The compound (IVA) was prepared by the thermal treatment of ammonium ZSM-5 at 500° C. for 4 hours. The mixture (II) and the compound (IV) were each pelletized, crushed, and sieved in a size of 100-300 μm separately. Both compounds were then added to the same tubular reactor but physically separated. First the mixture (II) was placed and packed into the reactor at the closer side to the reactor inlet, and then the compound (IVA) was placed into the reactor at the closer side to the reactor outlet. The catalyst beds of the two compounds were physically separated with quartz wool. The reaction mixture of hydrogen and $CO_2$ was then introduced into the tubular reactor at the total flow rate of 30 Nml/min at GHSV of ca. 10471 $h^{-1}$.

The reaction conditions of pressure, temperature, and molar ratio of hydrogen to carbon dioxide, as well as the carbon oxides per-pass conversion, and the amount of dimethyl ether obtained and its selectivity in the effluent stream are shown in Table 3.

Values of mmol of produced dimethyl ether per gram of the mixture (II) per hour are shown in Table 4.

TABLE 3

| Exp. No | $H_2/CO_2$ ratio | T (° C.) | P (bar) | $CO_2$ conv. (%) | Selectivity (mol %) | | | | |
|---|---|---|---|---|---|---|---|---|---|
| | | | | | DME | CO | $CH_4$ | MF | MeOH |
| 24[a,d,e] | 10:1 | 260 | 360 | 71.33 | 85.77 | 7.79 | 0.08 | 0.00 | 6.36 |
| 25[a,d,e] | 10:1 | 280 | 360 | 90.97 | 88.03 | 2.90 | 0.11 | 0.00 | 8.96 |
| 26[a,d,e] | 10:1 | 300 | 360 | 94.36 | 88.75 | 2.63 | 0.18 | 0.00 | 8.44 |
| 27[a,d,e] | 10:1 | 260 | 200 | 73.02 | 82.55 | 6.46 | 0.18 | 0.00 | 10.81 |
| 28[a,c,e] | 10:1 | 260 | 360 | 50.31 | 70.59 | 23.10 | 0.19 | 0.00 | 6.12 |
| 29[a,c,e] | 10:1 | 280 | 360 | 68.49 | 80.98 | 11.67 | 0.06 | 0.00 | 7.28 |
| 30[b,d,e] | 10:1 | 260 | 360 | 83.29 | 85.75 | 1.88 | 0.00 | 0.00 | 12.37 |
| 31[b,d,e] | 10:1 | 280 | 360 | 96.66 | 87.13 | 0.21 | 0.02 | 0.00 | 12.64 |
| 32[a,c,e] | 10:1 | 300 | 360 | 86.29 | 87.83 | 4.70 | 0.27 | 0.00 | 7.20 |
| 33[b,d,e] | 10:1 | 280 | 200 | 80.38 | 81.79 | 8.35 | 0.12 | 0.00 | 9.74 |
| 34[b,d,e] | 10:1 | 300 | 200 | 77.02 | 70.24 | 16.01 | 1.69 | 0.37 | 11.70 |
| 35[b,d,e] | 10:1 | 300 | 360 | 95.97 | 88.87 | 0.27 | 0.02 | 0.00 | 10.83 |
| 36[b,d,e] | 3:1 | 280 | 360 | 55.83 | 77.92 | 9.42 | 0.00 | 0.00 | 12.66 |
| 37[a,d,e] | 10:1 | 230 | 360 | 52.49 | 75.74 | 19.42 | 0.25 | 0.00 | 4.59 |
| 38[b,d,e] | 10:1 | 230 | 360 | 58.18 | 83.54 | 9.17 | 0.28 | 0.00 | 7.00 |
| 39[b,d,f] | 10:1 | 230 | 360 | 54.85 | 78.30 | 17.48 | 0.22 | 0.00 | 4.00 |
| 40[b,d,f] | 10:1 | 260 | 360 | 88.20 | 90.09 | 4.57 | 0.06 | 0.00 | 5.27 |
| 41[b,d,f] | 10:1 | 280 | 360 | 93.06 | 87.91 | 3.58 | 0.00 | 0.00 | 8.51 |
| 42[b,d,f] | 10:1 | 300 | 360 | 92.42 | 82.86 | 4.98 | 0.32 | 0.00 | 11.84 |
| 43[b,d,f] | 10:1 | 260 | 200 | 72.89 | 79.20 | 10.61 | 0.06 | 0.00 | 10.13 |

[a] the catalyst used is a mixture of 100 mg of the mixture (II) + 70 mg of the compound (IV).

[b] the catalyst used is a mixture of 170 mg of the mixture (II) + 170 mg of the compound (IV).

[c] the mixture (II) is the mixture (IIA).

[d] the mixture (II) is the mixture (IIB).

[e] the mixture (II) and the compound (IV) were pelletized, crushed and sieved separately and added as a physical mixture to the reactor (Procedure A: mixed bed)

[f] the mixture (II) and the compound (IV) were pelletized, crushed and sieved separately and were added to the same reactor but physically separated (Procedure B)

TABLE 4

| Exp. No | DME | CO | CH$_4$ | MF | MeOH |
|---|---|---|---|---|---|
| | | (mmol/g-cat · h) | | | |
| 24 | 23.90 | 2.17 | 0.02 | 0.00 | 1.77 |
| 25 | 31.28 | 1.03 | 0.04 | 0.00 | 3.18 |
| 26 | 32.70 | 0.97 | 0.07 | 0.00 | 3.11 |
| 27 | 23.52 | 1.81 | 0.05 | 0.00 | 3.14 |
| 28 | 13.89 | 4.52 | 0.04 | 0.00 | 1.20 |
| 29 | 21.67 | 3.12 | 0.02 | 0.00 | 1.95 |
| 30 | 27.90 | 0.61 | 0.00 | 0.00 | 4.02 |
| 31 | 32.88 | 0.08 | 0.01 | 0.00 | 4.78 |
| 32 | 29.60 | 1.58 | 0.09 | 0.00 | 2.42 |
| 33 | 25.67 | 2.59 | 0.04 | 0.00 | 3.09 |
| 34 | 20.94 | 4.87 | 0.54 | 0.12 | 3.61 |
| 35 | 33.31 | 0.10 | 0.01 | 0.00 | 4.06 |
| 36 | 47.33 | 5.72 | 0.00 | 0.00 | 7.70 |
| 37 | 15.52 | 3.98 | 0.05 | 0.00 | 0.95 |
| 38 | 18.98 | 2.07 | 0.07 | 0.00 | 1.61 |
| 39 | 16.78 | 3.74 | 0.05 | 0.00 | 0.85 |
| 40 | 31.04 | 1.57 | 0.02 | 0.00 | 1.81 |
| 41 | 31.95 | 1.30 | 0.00 | 0.00 | 3.09 |
| 42 | 29.91 | 1.80 | 0.12 | 0.00 | 4.26 |
| 43 | 22.56 | 2.95 | 0.02 | 0.00 | 2.93 |

Thus, the Examples illustrate the fact that the combination of the four technical features in the step of preparing methanol from carbon dioxide, that is a molar ratio of hydrogen to carbon dioxide equal to or higher than 3:1; a pressure equal to or higher than 200 bar; a temperature comprised of from 230 to 320° C.; and a space velocity comprised of from 5,000 to 20,000 h$^{-1}$, in the presence of a mixture (II) combined with the transformation of methanol into dimethyl ether in the presence of a compound (IV), results with a carbon oxides per-pass conversion equal to or higher than 50%, and a selectivity to methanol formation equal to or higher than 70%.

Process for the Preparation of a Mixture of ($C_2$-$C_8$)alkene and ($C_1$-$C_8$)alkane Examples 44-45

The synthesis of a mixture of ($C_2$-$C_8$)alkene and ($C_1$-$C_8$)alkane was carried out following the procedure as described in Examples 39-43 for the preparation of dimethyl ether, but using 170 mg of CuO/ZnO/$Al_2O_3$ (IIA), and 170 mg of H-ZSM-5 (VA) in a two-reactor system connected in series and a molar ratio of hydrogen to carbon dioxide of 10:1.

The first reactor for methanol synthesis contained (IIA), and the reaction was carried out at a temperature of 260° C. The second reactor for the ($C_2$-$C_8$)alkenes and ($C_1$-$C_8$)alkanes synthesis contained (VA) and the reaction was carried out at a temperature of 375° C.

The reaction mixture of hydrogen and $CO_2$ was then introduced into the tubular reactor (first reactor) at the total flow rate of 30 Nml/min at GHSV of ca. 10471 h$^{-1}$.

The pressure and the carbon oxides per-pass conversion, and the amount of various ($C_2$-$C_8$)alkenes and ($C_1$-$C_8$)alkanes and their selectivity in the effluent stream are shown in Table 5.

TABLE 5

| Exp. | $CO_2$ conv (%) | Selectivity | | | | | | | | | |
|---|---|---|---|---|---|---|---|---|---|---|---|
| | | CO | CH$_4$ | $C_2H_6$ | $C_2H_4$ | $C_3H_8$ | $C_3H_6$ | $C_4H_{10}$ | isobutane | MeOH | DME |
| 44[a] | 93.56 | 2.60 | 5.21 | 20.35 | 1.46 | 24.13 | 0 | 9.93 | 26.36 | 6.41 | 3.55 |
| 45[b] | 97.45 | 2.01 | 0.49 | 4.20 | 9.26 | 4.23 | 33.48 | 11.30 | 4.27 | 20.54 | 10.23 |

[a] Both reactors were operated at 360 bar, this pressure was regulated by the back pressure regulator placed after the second reactor containing compound (VA).
[b] The first reactor was operated at 360 bar and the second reactor was operated at atmospheric pressure. The effluent products of outlet of the back pressure regulator of the first reactor were directly passed into the second reactor at atmospheric pressure without any separation process between the pressure regulator and the reactor.

Stability Test of the Compound (IIA)
Reaction Conditions
Pressure: 360 bar;
Temperature: 260, and 280° C.;
Time: from 0 to 128 h
The Molar ratio of hydrogen to carbon dioxide was modified at given times of the experiment as indicated in Table 6.
Results
After carrying out the process for the preparation of methanol disclosed in the present invention under the reaction conditions mentioned above, no deactivation of the compound (IIA) was detected as shown in Table 6.

TABLE 6

| Time (h) | $H_2$/$CO_2$ ratio | T (° C.) | P (bar) | $CO_2$ conv. (%) | Selectivity (mol %) | | | | |
|---|---|---|---|---|---|---|---|---|---|
| | | | | | DME | CO | CH$_4$ | MF | MeOH |
| 0-20 | 3.6:1 | 280 | 360 | 69.98 | 0.00 | 14.20 | 0.62 | 0.00 | 85.19 |
| 20-43 | 3.6:1 | 280 | 360 | 70.67 | 0.00 | 14.55 | 0.71 | 0.00 | 84.75 |
| 43-60 | 9.98:1 | 280 | 360 | 94.49 | 0.46 | 3.24 | 0.69 | 0.00 | 95.60 |
| 60-84 | 5.84:1 | 280 | 360 | 86.98 | 0.44 | 9.67 | 1.10 | 0.00 | 88.79 |
| 84-96 | 7.84:1 | 280 | 360 | 91.39 | 0.43 | 5.63 | 1.08 | 0.00 | 92.86 |
| 96-100 | 1.11:1 | 280 | 360 | 26.70 | 0.26 | 38.80 | 0.00 | 0.26 | 60.68 |
| 100-113 | 9.98:1 | 280 | 360 | 94.13 | 0.49 | 3.45 | 0.99 | 0.00 | 95.07 |
| 113-120 | 9.98:1 | 280 | 360 | 94.25 | 0.48 | 3.57 | 1.19 | 0.00 | 94.76 |
| 120-128 | 9.98:1 | 260 | 360 | 95.17 | 0.00 | 2.18 | 0.49 | 0.00 | 97.33 |

Process for the Preparation of Methanol from Hydrogen and Carbon Dioxide

Examples 46 and 47 Using Mixture (IIA)

The process for preparing methanol is the same process as described for Examples 1-23, using the mixture (IIA) and carrying the process at a temperature of 260° C., at a pressure of 360 bar, and at a molar ratio of hydrogen to carbon dioxide of 10:1.

Values of GHSVs as well as the carbon oxides per-pass conversion, and the amount of methanol and its selectivity in the effluent stream are shown in Table 7.

TABLE 7

| Exp. | GHSV ($h^{-1}$) | $CO_2$ conv. (%) | Selectivity (mol %) | | | |
|---|---|---|---|---|---|---|
| | | | CO | $CH_4$ | MeOH | $CH_3OCH_3$ |
| 46 | 20,000 | 86.5 | 6.3 | 0.00 | 92.2 | 1.5 |
| 47 | 5,000 | 96.6 | 3.5 | 0.00 | 93.2 | 3.2 |

The results in Table 7 showed that the combination of the technical features in the step of preparing methanol from carbon dioxide, that is a molar ratio of hydrogen to carbon dioxide equal to or higher than 3:1; a pressure equal to or higher than 200 bar; a temperature comprised of from 230 to 320° C.; and a space velocity comprised of from 5,000 to 20,000 $h^{-1}$, allows obtaining methanol with both high carbon oxides per-pass conversion, high selectivity to methanol formation, and with an amount of methanol per mg of mixture (II) per hour higher than the ones described in the state of the art.

Process for the Preparation of Methanol from Hydrogen and Carbon Dioxide

Examples 48 to 53 Using Mixture (IIC)

A) General Procedure for the Activation of the Mixture (IIC)

Mixture (IIC), delivered as pellets by Alfa Aesar (catalog number 45776, lot number C18W019), was crushed and sieved to a size of 100-300 μm. The amount indicated in Table 8 of (IIC) was loaded in a tubular reactor and reduced in the stream of Argon (10 vol %) and $H_2$ (90 vol %) at 330° C. for 2 hours at atmospheric pressure. After the pre-reduction/activation step, the reactor was cooled down to room temperature.

i. Hydrogenation of Carbon Dioxide

A syringe pump was loaded with a compressed mixture of hydrogen, carbon dioxide and argon having a molar ratio $H_2:CO_2:Ar$ of 10:1:1.2. The feed gas mixture was then introduced into the reactor at different values of space velocity as indicated in Table 8. The pressure and temperature were regulated to be maintained in the reactor at 360 bar and 260° C. Then, the composition of the effluent stream was analyzed by gas chromatography.

ii. Results

The carbon oxides per-pass conversion, and the amount of methanol and its selectivity in the effluent stream are shown in Table 8.

Productivity of methanol and other products, expressed in millimoles of product per gram of the mixture (IIC), per hour are shown in Table 9.

TABLE 8

| Exp. | GHSV ($h^{-1}$) | cat weight/ mg | $CO_2$ conv (%) | Selectivity (mol %) | | | | |
|---|---|---|---|---|---|---|---|---|
| | | | | DME | CO | $CH_4$ | MF | MeOH |
| 48 | 10000 | 85 | 95.79 | 0.00 | 1.44 | 0.00 | 0.00 | 98.56 |
| 49 | 20000 | 85 | 95.65 | 0.00 | 1.77 | 0.00 | 0.00 | 98.23 |
| 50 | 40000 | 85 | 89.94 | 0.00 | 4.85 | 0.00 | 0.00 | 95.15 |
| 51 | 81000 | 42.5 | 78.83 | 0.00 | 10.28 | 0.00 | 0.00 | 89.72 |
| 52 | 131000 | 42.5 | 71.79 | 0.00 | 19.89 | 0.00 | 0.00 | 80.11 |
| 53 | 182000 | 42.5 | 65.80 | 0.00 | 22.73 | 0.00 | 0.00 | 77.27 |

TABLE 9

| Exp. | mmol/g-cat · h | | | | |
|---|---|---|---|---|---|
| | DME | CO | $CH_4$ | MF | MeOH |
| 48 | 0.00 | 0.04 | 0.00 | 0.00 | 24.62 |
| 49 | 0.00 | 0.88 | 0.00 | 0.00 | 48.83 |
| 50 | 0.00 | 4.56 | 0.00 | 0.00 | 89.20 |
| 51 | 0.00 | 16.87 | 0.00 | 0.00 | 147.48 |
| 52 | 0.00 | 48.38 | 0.00 | 0.00 | 194.89 |
| 53 | 0.00 | 70.19 | 0.00 | 0.00 | 238.55 |

The results in Tables 8 and 9 showed that the process of the invention allows obtaining methanol with both a high carbon oxides per-pass conversion, high selectivity to methanol formation, and with an amount of methanol per gram of mixture (II) per hour higher than the ones described in the state of the art.

Thus, the Examples illustrate the fact that the combination of the four technical features, that is a molar ratio of hydrogen to carbon dioxide equal to or higher than 3:1; a pressure comprised equal to or higher than 200 bar; a temperature comprised of from to 320° C.; and a space velocity comprised of from 5,000 to 200,000 $h^{-1}$ in the presence of a mixture (II) results in a process for preparing methanol with a carbon oxides per-pass conversion equal to or higher than 65%, and a selectivity to methanol formation equal to or higher than 75%.

The invention claimed is:

1. A process for the preparation of methanol, with a carbon oxides per-pass conversion equal to or higher than 65%, and selectivity to methanol formation equal to or higher than 75%, comprising reacting hydrogen with carbon dioxide, carbon monoxide or mixtures thereof; at a pressure equal to or higher than 200 bar; at a temperature comprised of from 230 to 320° C.; and at a space velocity comprised of from 5,000 to 200,000 $h^{-1}$ in the presence of a mixture (I) comprising $M_1$ and $M_2$, or alternatively, in the presence of a mixture (II) comprising $M_1$, $M_2$ and at least a compound of formula $A_nO_m$; or alternatively, in the presence of a mixture (III) comprising $M_1$ and at least a compound of formula $A_nO_m$, wherein:
the molar ratio of hydrogen to carbon dioxide, the molar ratio of hydrogen to the mixture of carbon dioxide and carbon monoxide, or the molar ratio of hydrogen to carbon monoxide is equal to or higher than 3:1;
$M_1$ is Cu, CuO, $Cu_2O$ or a mixture thereof;
$M_2$ is Zn, ZnO or a mixture thereof;
A is a cation selected from the group consisting of $Mg^{2+}$, $Al^{3+}$, $Si^{2+}$, $Si^{4+}$, $Ti^{3+}$, $Ti^{4+}$, $V^{2+}$, $V^{3+}$, $V^{4+}$, $V^{5+}$, $Cr^{2+}$, $Cr^{3+}$, $Zr^{4+}$, $Mn^{2+}$, $Mn^{3+}$, $Mn^{4+}$, $Mn^{6+}$, $La^{3+}$, $Ce^{3+}$, $Ce^{4+}$, and $Th^{4+}$; and n is an integer selected from 1 to 3; m is an integer selected from 1 to 9; the sum of positive charges of $A_n$ being equal to the sum of negative charges of $O_m$.

2. The process according to claim 1, wherein the mixture (I), or alternatively the mixture (II), or alternatively the mixture (III) are mixtures obtainable by co-precipitation.

3. The process according to claim 2, wherein $M_1$ is selected from Cu, CuO and a mixture thereof; $M_2$ is selected from Zn, ZnO, and a mixture thereof, and A is selected from $Mg^{2+}$, $Al^{3+}$, and a mixture thereof.

4. The process according to claim 3, wherein:
the process for the preparation of methanol is carried out in the presence of the mixture (I) comprising $M_1$ and $M_2$ obtainable by a process comprising: (a) contacting CuX, and ZnY with a base to form a precipitate; (b) filtering, washing, and drying the precipitate obtained in step (a) to form a solid; and (c) calcining the solid obtained in step (b); or alternatively,
the process for the preparation of methanol is carried out in the presence of the mixture (II) comprising $M_1$, $M_2$ and at least a compound of formula $A_nO_m$, obtainable by a process comprising: (a') contacting CuX, ZnY, and AZ with a base to form a precipitate; (b') filtering, washing, and drying the precipitate obtained in step (a') to form a solid; and (c') calcining the solid obtained in step (b'); or alternatively,
the process for the preparation of methanol is carried out in the presence of the mixture (III) comprising $M_1$ and at least a compound of formula $A_nO_m$, obtainable by the process comprising: (a") contacting CuX, and AZ with a base to form a precipitate; (b") filtering, washing, and drying the precipitate obtained in step (a") to form a solid; and (c") calcining the solid obtained in step (b"),
wherein X, Y, and Z are each an anion independently selected from the group consisting of $NO_3^-$, $Cl^-$, $Br^-$, $F^-$, $I^-$, $CO_3^{2-}$, $HCO_3^-$, $SO_4^{2-}$, $CH_3COO^-$, $C_2O_4^{2-}$, $CN^-$ and tartrate.

5. The process according to claim 4, wherein in step (a), (a'), or (a") X, Y, and Z are $NO_3^-$, and the base is KOH.

6. The process according to claim 5, wherein step (a), (a'), or (a") is carried out at a temperature comprised from 60 to 95° C.

7. The process according to claim 6, wherein step (c), (c'), or (c") is carried out at a pH comprised from 8 to 11.

8. The process according to claim 3, wherein the carbon oxides per-pass conversion is equal to or higher than 65%, the selectivity to methanol formation is equal to or higher than 80%, and the space velocity is comprised of from 5,000 to 20,000 $h^{-1}$.

9. The process according to claim 8, wherein the process is carried out at a pressure comprised of from 200 to 1000 bar, and the molar ratio of hydrogen to carbon dioxide, the molar ratio of hydrogen to the mixture of carbon dioxide and carbon monoxide, or the molar ratio of hydrogen to carbon monoxide is comprised of from 3:1 to 20:1.

10. The process according to claim 9, wherein the molar ratio of hydrogen to carbon dioxide, the molar ratio of hydrogen to the mixture of carbon dioxide and carbon monoxide, or the molar ratio of hydrogen to carbon monoxide is comprised from 7:1 to 20:1; the process is carried out at a pressure comprised of from 350 to 400 bar; the temperature of the process for preparing methanol is comprised from 240 to 300° C.; and wherein the process is carried out in a fixed bed reactor.

11. The process according to claim 10, wherein the process is carried out by reacting hydrogen with carbon dioxide.

12. The process according to claim 11, wherein the process for the preparation of methanol is carried out in the presence of the mixture (I), or alternatively, in the presence of the mixture (II), or alternatively, in the presence of the mixture (III) wherein $M_1$ is comprised from 20 to 90% by weight.

13. The process according to claim 12, wherein the process for the preparation of methanol is carried out in the presence of the mixture (II) wherein $M_1$ is comprised from 20 to 90% by weight and $A_nO_m$ is comprised from 4 to 50% by weight.

14. The process according to claim 13, wherein the mixture (II) is:
the mixture (IIA) wherein $M_1$ is CuO, $M_2$ is ZnO, and A is Al, the content of $M_1$ is 29% by weight, the content of $M_2$ is 28% by weight, and the content of $Al_2O_3$ is 43% by weight; or alternatively,
the mixture (IIB) wherein $M_1$ is CuO, $M_2$ is ZnO, and A is Al, the content of $M_1$ is 48% by weight, the content of $M_2$ is 47% by weight, and the content of $Al_2O_3$ is 5% by weight; or alternatively,
the mixture (IIC) wherein $M_1$ is CuO, $M_2$ is ZnO, and A is Al, the content of $M_1$ is 63.5% by weight, the content of $M_2$ is 24.7% by weight, and the content of $Al_2O_3$ is 10.1% by weight; and wherein mixture (IIC) further comprises MgO, and the content of MgO is 1.3% by weight.

15. The process according to claim 12, wherein the mixture (III) is the mixture (IIIA) wherein $M_1$ is CuO, A is Al, the content of $M_1$ is 45% by weight, and the content of $Al_2O_3$ is 55% by weight.

16. The process according to claim 14, having a carbon oxides per-pass conversion equal to or higher than 90%, and a selectivity to methanol formation equal to or higher than 80%, wherein: the process is carried out at a pressure comprised of from 350 to 400 bar; at a temperature comprised of from 250 to 320° C.; and the molar ratio of hydrogen to carbon dioxide is comprised of from 8:1 to 20:1.

17. The process according to claim 14, having a carbon oxides per-pass conversion equal to or higher than 95%, and selectivity to methanol formation equal to or higher than 98%, wherein: the process is carried out at a pressure comprised of from 350 to 400 bar; at a temperature comprised of from 250 to 300° C.; and the molar ratio of hydrogen to carbon dioxide is comprised of from 10:1 to 20:1.

18. The process according to claim 14, further comprising converting the methanol to dimethyl ether, with a carbon oxides per-pass conversion equal to or higher than 50%, and a selectivity to dimethyl ether formation equal to or higher than 70%, in the presence of a compound (IV) selected from the group consisting of alumina, silica-alumina, natural zeolites, synthetic alumino-silicate zeolite, and alumino-phospho-silicates.

19. The process according to claim 18, wherein the process of converting the methanol to dimethyl ether is carried out at a temperature comprised of from 230 to 320° C.; at a pressure comprised of from 350 to 400 bar; the molar ratio of hydrogen to carbon dioxide, the molar ratio of hydrogen to the mixture of carbon dioxide and carbon monoxide, or the molar ratio of hydrogen to carbon monoxide is 10:1; and wherein the compound (IV) is a synthetic alumino-silicate zeolite.

20. The process according to claim 14, further comprising converting the methanol to a mixture of $(C_2-C_8)$alkene and $(C_1-C_8)$alkane, in the presence of a compound (IV) selected from the group consisting of synthetic alumino-silicate zeolite, and alumino-phospho-silicates at a temperature comprised of from higher than 320 to 600° C.; and at a pressure comprised of from 1 to 400 bar.

21. The process according to claim 20, wherein when the process is carried out at a pressure comprised of from 200 to 400 bar, then the mixture of ($C_2$-$C_8$)alkene and ($C_1$-$C_8$)alkane is a mixture enriched in ($C_1$-$C_8$)alkane; or alternatively, when the process is carried out at a pressure comprised of from 1 to 10 bar, then the mixture of ($C_2$-$C_8$)alkene and ($C_1$-$C_8$)alkane is a mixture enriched in ($C_2$-$C_8$)alkene.

22. The process according to claim 21, wherein the compound (IV) is a synthetic alumino-silicate zeolite.

\* \* \* \* \*